US011395714B2

(12) United States Patent
Mullani et al.

(10) Patent No.: US 11,395,714 B2
(45) Date of Patent: Jul. 26, 2022

(54) MEDICAL ILLUMINATOR WITH VARIABLE POLARIZATION

(71) Applicant: DermLite LLC, San Juan Capistrano, CA (US)

(72) Inventors: Nizar Mullani, Sugar Land, TX (US); Thorsten Trotzenberg, Wiesbaden (DE); Gregory Paul Lozano-Buhl, Grand Rapids, MI (US)

(73) Assignee: DermLite LLC, San Juan Capistrano, CA (US)

( * ) Notice: Subject to any disclaimer, the term of this patent is extended or adjusted under 35 U.S.C. 154(b) by 26 days.

(21) Appl. No.: 17/093,467

(22) Filed: Nov. 9, 2020

(65) Prior Publication Data
US 2021/0137633 A1 May 13, 2021

Related U.S. Application Data

(60) Provisional application No. 62/933,883, filed on Nov. 11, 2019.

(51) Int. Cl.
*A61B 90/00* (2016.01)
*H05B 45/325* (2020.01)
(Continued)

(52) U.S. Cl.
CPC .......... *A61B 90/36* (2016.02); *F21V 9/14* (2013.01); *F21V 23/04* (2013.01); *G02B 25/002* (2013.01);
(Continued)

(58) Field of Classification Search
CPC ..... A61B 90/36; A61B 5/0077; A61B 5/1032; A61B 5/441; A61B 5/0059; A61B 5/0064;
(Continued)

(56) References Cited

U.S. PATENT DOCUMENTS 1,774,331 A    8/1930   Koller
1,786,420 A    12/1930   Braly
(Continued)

FOREIGN PATENT DOCUMENTS

EP    1427474    6/2004
IT    01300568    10/1999
(Continued)

OTHER PUBLICATIONS

"Extended European Search Report," European Patent Application No. 20206915.9-1113, dated Feb. 25, 2021, 10 pages, European Patent Office, Munich, Germany.
(Continued)

*Primary Examiner* — Rajarshi Chakraborty
*Assistant Examiner* — Glenn D Zimmerman
(74) *Attorney, Agent, or Firm* — Stetina Brunda Garred and Brucker

(57) ABSTRACT

A device for variable polarization by an illumination device for illuminating organic tissue. The device includes a first set of one or more light emitting diodes (LEDs), a first polarizer arranged to polarize light emitted from the first set of LEDs in a first polarization direction, a second set of one or more LEDs, a second polarizer arranged to polarize light emitted from the second set of LEDs in a second polarization direction. A lens is arranged to collect light from organic tissue illuminated by the first and/or second sets of LEDs including a viewing polarizer arranged to polarize the light collected from the organic tissue in the second polarization direction. A signal generator is operable to signal one or more drivers for driving one of the first and second sets according a signal value and driving the other of the first and second sets according to an inverse value thereof.

15 Claims, 16 Drawing Sheets

(51) Int. Cl.
  *F21V 9/14* (2006.01)
  *F21V 23/04* (2006.01)
  *G02B 25/00* (2006.01)
  *F21Y 115/10* (2016.01)
  *G02B 7/02* (2021.01)

(52) U.S. Cl.
  CPC ........ *H05B 45/325* (2020.01); *F21Y 2115/10* (2016.08); *G02B 7/02* (2013.01)

(58) Field of Classification Search
  CPC ... A61B 2090/3616; F21V 9/14; F21V 23/04; G02B 25/002; G02B 7/02; G02B 5/3025; G02B 25/007; G02B 25/008; G02B 25/02; H05B 45/325; F21Y 2115/10
  See application file for complete search history.

(56) References Cited

U.S. PATENT DOCUMENTS

| | | |
|---|---|---|
| 2,120,365 A | 6/1938 | Kriebel |
| 2,866,375 A | 12/1958 | Wells et al. |
| 2,947,212 A | 8/1960 | Woods et al. |
| 3,062,087 A | 11/1962 | Zandman et al. |
| 3,519,339 A | 7/1970 | Hutchinson et al. |
| 3,711,182 A | 1/1973 | Jasgur |
| 4,007,979 A | 2/1977 | Coblitz |
| 4,070,096 A | 1/1978 | Jasgur |
| 4,398,541 A | 8/1983 | Pugliese |
| 4,538,889 A | 9/1985 | Heine et al. |
| 4,773,097 A | 9/1988 | Suzaki et al. |
| 4,846,184 A | 7/1989 | Comment et al. |
| 4,957,368 A | 9/1990 | Smith |
| 4,988,158 A | 1/1991 | Yamamoto |
| 4,998,818 A | 3/1991 | Kugler et al. |
| 5,146,923 A | 9/1992 | Dhawan |
| 5,198,875 A | 3/1993 | Bazin et al. |
| 5,343,536 A | 8/1994 | Groh |
| 5,363,854 A | 11/1994 | Martens et al. |
| 5,442,488 A | 8/1995 | Pastorino |
| 5,442,489 A | 8/1995 | Yamamoto et al. |
| 5,492,118 A | 2/1996 | Gratton et al. |
| 5,561,563 A | 10/1996 | Chestnut et al. |
| 5,690,417 A | 11/1997 | Polidor et al. |
| 5,742,392 A | 4/1998 | Anderson et al. |
| 5,760,407 A | 6/1998 | Margosiak et al. |
| 5,900,996 A | 5/1999 | Zadro |
| 6,032,071 A | 2/2000 | Binder |
| D425,313 S | 5/2000 | Zadro |
| 6,069,565 A | 5/2000 | Stern et al. |
| 6,081,612 A | 6/2000 | Gutkowicz-Krusin et al. |
| 6,118,476 A | 9/2000 | Morito et al. |
| 6,158,877 A | 12/2000 | Zadro |
| 6,207,136 B1 | 3/2001 | Matsuoka |
| 6,384,988 B1 | 5/2002 | Muller et al. |
| 6,396,532 B1 | 5/2002 | Hoover et al. |
| 6,483,247 B2 | 11/2002 | Edwards et al. |
| 6,587,711 B1 | 7/2003 | Alfano et al. |
| 6,842,635 B1 | 1/2005 | Parker |
| 7,004,599 B2 | 2/2006 | Mullani |
| 7,006,223 B2 | 2/2006 | Mullani |
| 7,027,153 B2 | 4/2006 | Mullani |
| 7,151,956 B2 | 12/2006 | Satoh et al. |
| 7,167,243 B2 | 1/2007 | Mullani |
| 7,167,244 B2 | 1/2007 | Mullani |
| 7,220,254 B2 | 5/2007 | Altshuler et al. |
| 7,400,918 B2 | 7/2008 | Parker et al. |
| 7,621,653 B2 | 11/2009 | Hendrie |
| 7,841,751 B2 | 11/2010 | Mulani |
| 7,874,698 B2 | 1/2011 | Mullani |
| 7,986,987 B2 | 7/2011 | Bazin et al. |
| 8,496,695 B2 | 7/2013 | Kang et al. |
| 8,498,460 B2 | 7/2013 | Patwardhan |
| 8,588,605 B2 | 11/2013 | Harris |
| 8,677,829 B2 | 3/2014 | Shahzad et al. |
| 8,849,380 B2 | 9/2014 | Patwardhan |
| 9,055,867 B2 | 6/2015 | Fox et al. |
| 9,182,343 B2 | 11/2015 | Goldfain |
| 9,314,149 B2 | 4/2016 | Vivenzio et al. |
| 9,345,430 B2 | 5/2016 | Nakamura et al. |
| 9,427,188 B2 | 8/2016 | Heine et al. |
| 9,445,713 B2 | 9/2016 | Douglas et al. |
| 9,458,990 B2 | 10/2016 | Mullani |
| 9,642,517 B2 | 5/2017 | Wood et al. |
| 9,928,592 B2 | 3/2018 | Xiong et al. |
| 10,130,260 B2 | 11/2018 | Patwardhan |
| 10,156,710 B2 | 12/2018 | Anhut et al. |
| 10,201,268 B2 | 2/2019 | Harris |
| 10,209,500 B2 | 2/2019 | Huang et al. |
| 10,278,636 B2 | 5/2019 | Wu et al. |
| 10,368,795 B2 | 8/2019 | Patwardhan |
| 10,405,752 B2 | 9/2019 | Khosravi Simchi et al. |
| 10,441,379 B2 | 10/2019 | Mullani |
| 10,502,942 B2 | 12/2019 | Todd et al. |
| 10,537,248 B2 | 1/2020 | Hong |
| 10,539,463 B2 | 1/2020 | Hwang et al. |
| 10,542,928 B2 | 1/2020 | Houjou et al. |
| 10,551,248 B2 | 2/2020 | Jang et al. |
| 10,558,035 B2 | 2/2020 | Shen et al. |
| 10,617,305 B2 | 4/2020 | Patwardhan et al. |
| 10,667,694 B2 | 6/2020 | Khosravi Simchi et al. |
| 10,932,669 B2 | 3/2021 | Shinozaki |
| 2003/0026110 A1 | 2/2003 | Satoh et al. |
| 2003/0045799 A1 | 3/2003 | Bazin et al. |
| 2004/0062056 A1 | 4/2004 | Heine et al. |
| 2004/0174525 A1 | 9/2004 | Mullani |
| 2004/0201846 A1 | 10/2004 | Mullani |
| 2006/0122515 A1 | 6/2006 | Zeman et al. |
| 2008/0015663 A1 | 1/2008 | Mullani |
| 2008/0065176 A1 | 3/2008 | Zhang et al. |
| 2008/0132794 A1 | 6/2008 | Alfano et al. |
| 2009/0093761 A1 | 4/2009 | Sliwa et al. |
| 2010/0026785 A1* | 2/2010 | Soto-Thompson .. A61B 5/0084 348/47 |
| 2011/0270200 A1 | 11/2011 | Edgar et al. |
| 2011/0304705 A1 | 12/2011 | Kantor et al. |
| 2013/0109977 A1 | 5/2013 | Nikzad et al. |
| 2014/0012137 A1 | 1/2014 | Rosen |
| 2014/0243685 A1* | 8/2014 | Patwardhan ............. A61B 5/44 600/476 |
| 2014/0267882 A1 | 9/2014 | O'Neill et al. |
| 2014/0364745 A1 | 12/2014 | Patwardhan |
| 2015/0073227 A1 | 3/2015 | Teder et al. |
| 2015/0126981 A1 | 5/2015 | Verghese et al. |
| 2015/0374277 A1 | 12/2015 | Patwardhan |
| 2016/0282593 A1 | 9/2016 | Yan |
| 2016/0290925 A1 | 10/2016 | Takahashi |
| 2016/0296112 A1 | 10/2016 | Fletcher et al. |
| 2016/0339218 A1 | 11/2016 | Casasanta, III et al. |
| 2017/0126943 A1 | 5/2017 | Fletcher et al. |
| 2017/0303857 A1 | 10/2017 | Perkins et al. |
| 2017/0336619 A1 | 11/2017 | Cheng |
| 2018/0140196 A1 | 5/2018 | Khosravi Simchi et al. |
| 2018/0279942 A1 | 10/2018 | Houjoi et al. |
| 2018/0289269 A1 | 10/2018 | Choi et al. |
| 2018/0310872 A1 | 11/2018 | Tseng et al. |
| 2018/0368692 A1* | 12/2018 | Hong .................. A61B 5/0077 |
| 2019/0133513 A1 | 5/2019 | Patwardhan |
| 2019/0201156 A1* | 7/2019 | Mullani ............. A61B 90/361 |
| 2019/0343396 A1 | 11/2019 | Khosravi Simchi et al. |
| 2019/0343450 A1 | 11/2019 | Park |
| 2020/0060608 A1 | 2/2020 | Choi |
| 2020/0100722 A1 | 4/2020 | Pikkula et al. |
| 2020/0367803 A1 | 11/2020 | Witkowski et al. |
| 2021/0059533 A1* | 3/2021 | Patwardhan ......... A61B 5/0077 |
| 2021/0145251 A1 | 5/2021 | Rusoke-Dierich |
| 2021/0265060 A1 | 8/2021 | Aoki et al. |

FOREIGN PATENT DOCUMENTS

| | | |
|---|---|---|
| JP | 04214523 | 8/1992 |
| JP | 4667313 | 4/2011 |
| WO | 2007034525 | 3/2007 |
| WO | 2014105649 | 7/2014 |

(56) References Cited

FOREIGN PATENT DOCUMENTS

| WO | 2015035229 | 3/2015 |
|---|---|---|
| WO | 2019074298 | 4/2019 |
| WO | 2020000055 | 1/2020 |

OTHER PUBLICATIONS

Kapsokalyvas, Dimitrios et al., "Spectral morphological analysis of skin lesions with a polarization multispectral dermoscope", Feb. 20, 2013, 4826-4840, vol. 21, No. 4, Optics Express.
Wang, Hening et al., "Systematic Design of a Cross-Polarized Dermoscope for Visual Inspection and Digital Imaging," IEEE Instrumentation & Measurement Magazine, pp. 26-31, Dec. 2011.
"The physical basis for skin appearance is reflectance of light," (Internet Literature), www.syrisscientific.com, 1 page, Web printout Feb. 24, 2003.
(Instruction Manual—English Portion) "DermLite DL100", 3Gen, LLC., 2008 (1 page).
(Instruction Manual—English Portion) "DermLite carbon", 3Gen, LLC., 2008 (1 page).
(Instruction Manual—English Portion) "DermLite cam Dermoscopy Camera", 3Gen, Inc., 2013 (1 page).
(Instruction Manual—English Portion) "DermLite II PRO HR", 3Gen, LLC., 2008 (1 page).
(Instruction Manual—English Portion) "DermLite II Pro", 3Gen, LLC., 2007 (1 page).
(Instruction Manual—English Portion) "DermLite DL3", 3Gen, LLC., 2009 (1 page).
(Instruction Manual—English Portion) "DermLite II Multispectral", 3Gen, LLC., 2004 (1 page).
(Instruction Manual—English Portion) "Lumio DermLite", 3Gen, LLC., 2007 (1 page).
(Instruction Manual—English Portion) "DermLite Foto Quickstart Guide", 3Gen, LLC., 2009 (1 page).
Barun, Vladimir V. et al., "Absorption spectra and light penetration depth of normal and pathologically altered human skin", ResearchGate, (Website) Journal of Applied Spectroscopy, vol. 74 (No. 3), Mar. 2007 (11 pages). https://www.researchgate.net/publication/225598882.
Keshen R. Mathura et al., "Comparison of OPS imaging and conventional capillary microscopy to study the human microcirculation," The American Physiological Society, vol. 91, p. 74-78, 2001 (5 pages).
(Instruction Manual—English Portion) "DermLite II Fluid", 3Gen, LLC., 2006 (1 page).
(Instruction Manual—English Portion) "DermLite II Hybrid m", 3Gen, LLC., 2009 (1 page).
(Brochure) 3Gen, LLC., "First in Pocket Epiluminescence Microscopy," 1 page, Mar. 15, 2001 (Estimated publication date).
(Brochure) 3Gen, LLC., "3Gen the Beauty of Revolutionary Innovation," 3 pages (trifold), Feb. 15, 2002 (Estimated publication date) (6 pages).
(Instruction Manual—English Portion) "DermLite DL1", 3Gen, LLC., 2011 (1 page).
Pan, Yan et al., "Polarized and Nonpolarized Dermoscopy The Explanation for the Observed Differences", American Medical Society, (Reprinted) Arch Dermatol, vol. 144 (No. 6), Jun. 2008 (2 pages).
(Instruction Manual—English Portion) "Lumio—Dermlite," 3Gen, Inc., 2015, 3 pages.
Dermlite Website, "Lumio," https://dermlite.com/collections/lumio-scopes/products/lumio, publication date unknown, site visited Jan. 18, 2021.
Dermlite Website, "Lumio S," https://dermlite.com/collections/lumio-scopes/products/lumio-s, publication date unknown, site visited Jan. 18, 2021.
(Instruction Manual—English Portion) "Dermlite Lumio S," 3Gen, Inc., 2014, 3 pages.
(Instruction Manual—English Portion) "Dermlite Lumio S," 3Gen, Inc., 2013, 1 page.
(Instruction Manual—English Portion) "Dermlite Lumio UV," 3Gen, Inc., 2014, 3 pages.
Dermlite Website, "Lumio UV," https://dermlite.com/collections/lumio-scopes/products/lumio-uv, publication date unknown, site visited Jan. 18, 2021.
Dhawan, Atam P. et al., "Multispectral Optical Imaging of Skin-Lesions for Detection of Malignant Melanomas", 31st Annual International Conference of the IEEE EMBS, Minneapolis, MN, USA, Sep. 2-6, 2009, p. 5352-5355, 2009, (4 pages).
Arrazola, Peter et al., "Dermlite II: An Innovative Portable Instrument for Dermoscopy Without the Need of Immersion Fluids", Skin Med, Le Jacq Mar.-Apr. 2005; 10: p. 78-83 (6 pages).
Garcia-Uribe, Alejandro et al., "In-vivo characterization of optical properties of pigmented skin lesions including melanoma using oblique incidence diffuse reflectance spectrometry", Journal of Biomedical Optics, vol. 16 (2), p. 020501-1-020501-3, Feb. 2011 (3 pages).
Goggle Search, "Orange light wavelength range," 2 pages search results, multiple sources.
Thong, Foo Hong, "Advantages of an Optical Encoder," https://www.digikey.com/en/articles/advantages-of-an-optical-encoder. May 6, 2011, 6 pages, Convergence Promotions LLC.
Data Sheet, Avago Technologies, "AEDR-8300-1Wx Encoders," Sep. 9, 2013, 8 pages.
Susmita Sridhar, Anabela Da Silva. "Enhanced contrast and depth resolution in polarization imaging using elliptically polarized light," Journal of Biomedical Optics, Society of Photo-optical Instrumentation Engineers, 2016, 21 (7), 10.1117/1.JBO.21.7.071107. hal-01280108.
Jacques, Steven L. et al., "Imaging Superficial Tissues with Polarized Light," Lasers in Surgery and Medicine, 26:119-129 (2000), Wiley-Liss, Inc.
Jacques, Steven L., "Imaging skin pathology with polarized light," Journal of Biomedical Optics 7(3), 329-340 (Jul. 2002).
Jacques, Steven L., "Corrigendum: Optical properties of biological tissues: a review," Physics in Medicine and Biology, 58 (2013) 5007-5008, Institute of Physics and Engineering in Medicine.
"Stokes parameters," Wikipedia, https://en.wikipedia.org/wiki/Stokes_parameters, last edited May 27, 2020, 9 pages.
4D Technology, "Polarimetry," https://www.4dtechnology.com/applications/polarimetry/, web printout Nov. 5, 2020, 7 pages.
Rioux, Frank, "Polarized Light and Quantum Superposition," Last updated Aug. 15, 2020, Retrieved Oct. 23, 2020, https://chem.libretexts.org/@go/page/138799, 2 pages.
(Flyer), Visiomed, "MicroDERM Luminis The hand-held dermoscope with daylight optics", Visiomed AG 2009, (2 pages).
(Marketing Slide), 3Gen, "DermLite Platinum," 2002, 3Gen, LLC, 1 page.

* cited by examiner

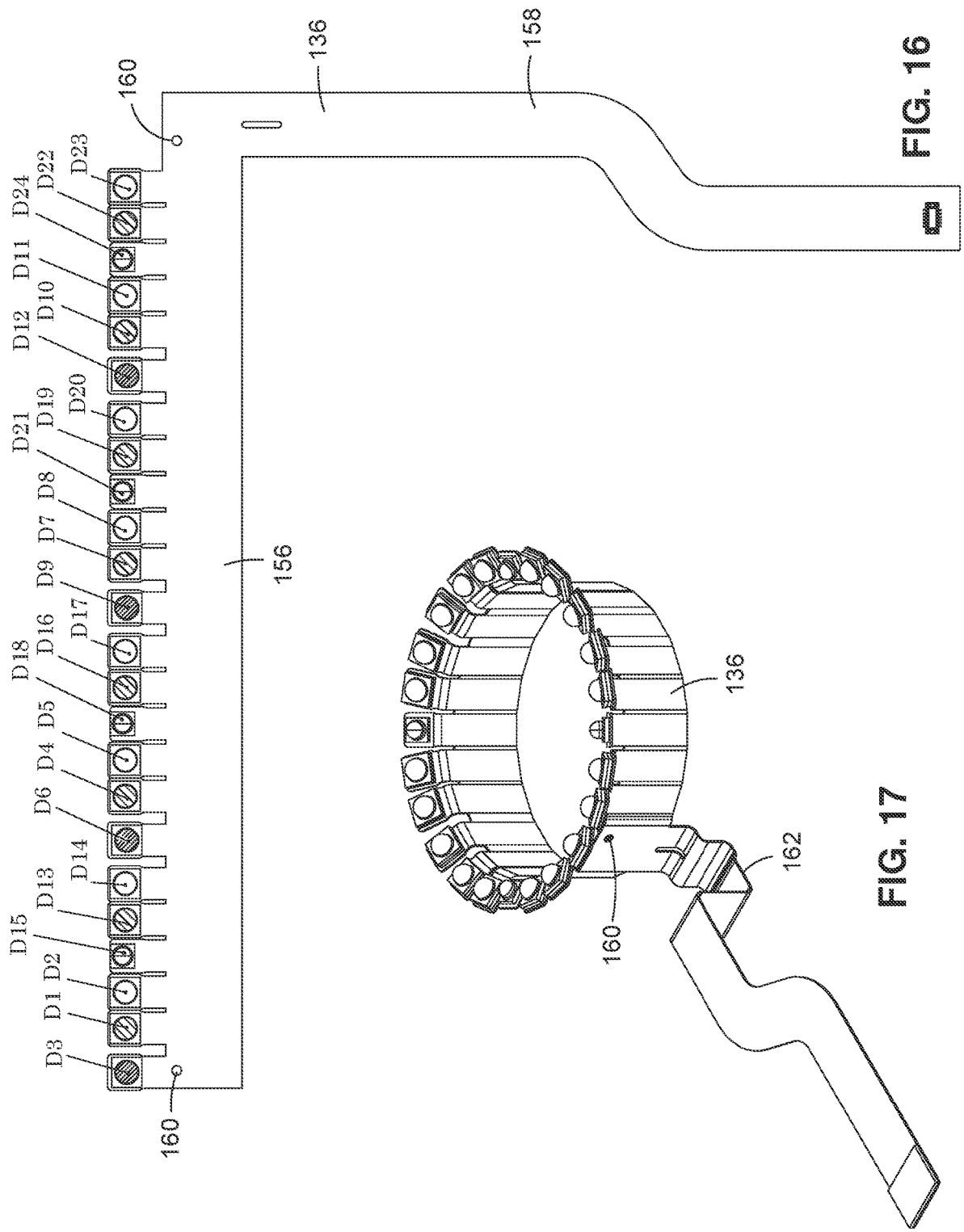

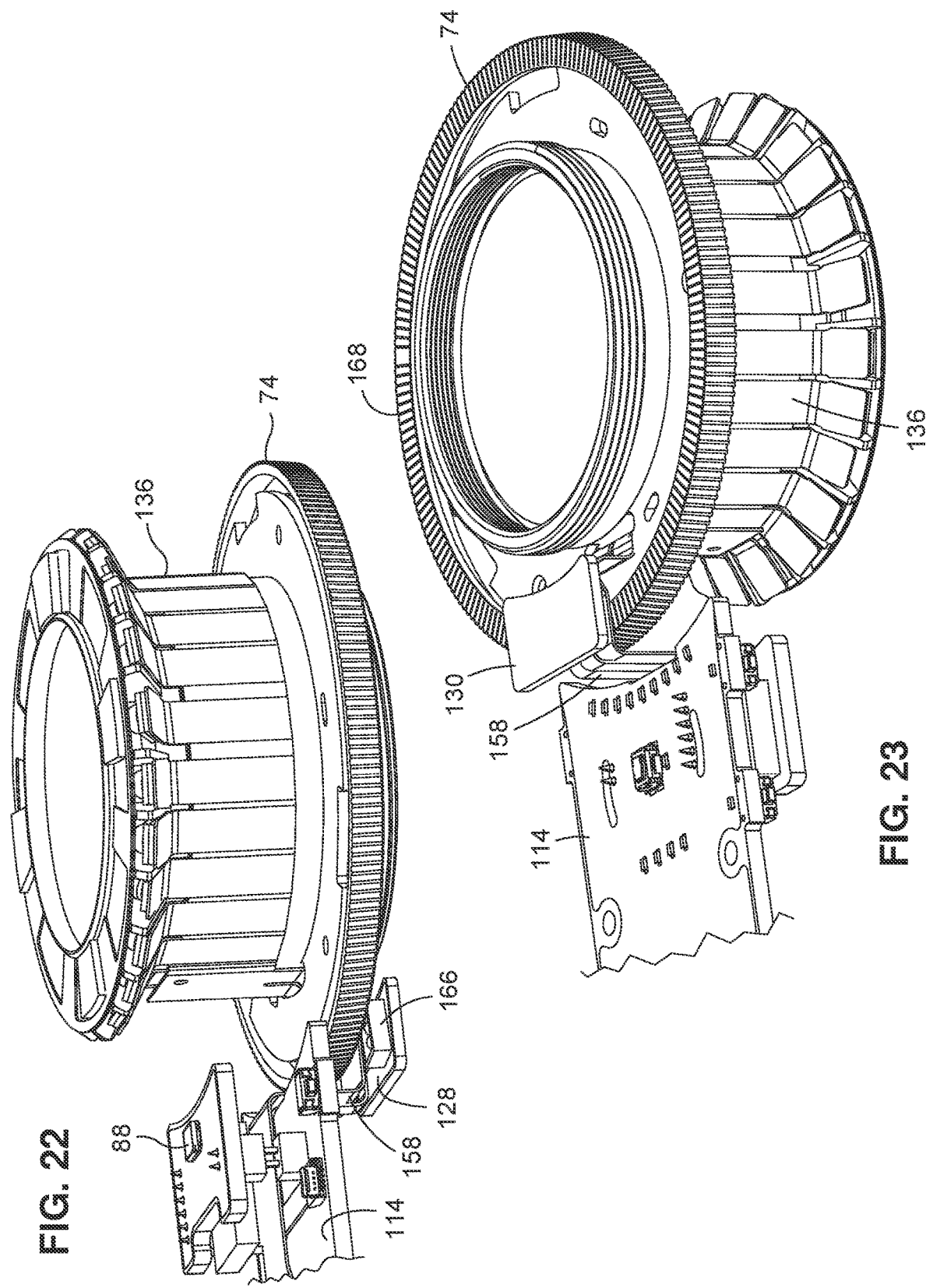

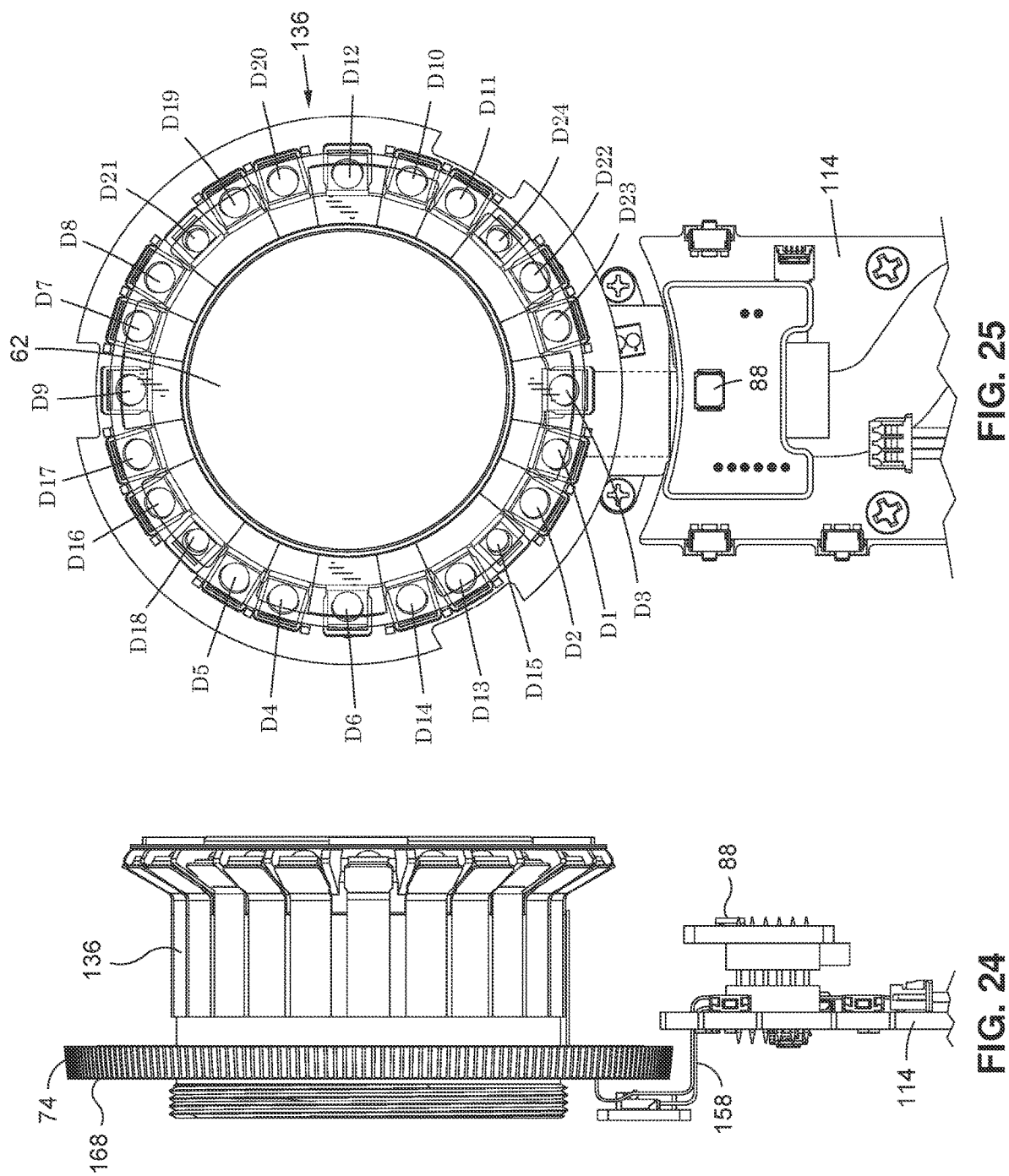

MEDICAL ILLUMINATOR WITH VARIABLE POLARIZATION

CROSS-REFERENCE TO RELATED APPLICATIONS

This application relates to and claims the benefit of U.S. Provisional Patent Application Ser. No. 62/933,883, filed Nov. 11, 2019 and entitled "MEDICAL ILLUMINATOR WITH VARIABLE POLARIZATION," the entire contents of which is hereby incorporated by reference.

STATEMENT RE: FEDERALLY SPONSORED RESEARCH/DEVELOPMENT

Not Applicable

BACKGROUND

Technical Field

The present disclosure relates generally to a hand-held illumination device used in medical examinations. More particularly, the present disclosure relates to an improved apparatus for enhanced viewing and illumination for medical examinations using cross-polarized and parallel-polarized light to aid in viewing internal structures as well as the skin surface.

Background

Medical examinations by physicians may employ the use of hand-held illuminators to assist the doctor in magnified and non-magnified viewing of the tissue of a patient. Hand-held illuminators without magnification include pen lights, which are widely used by general medical practitioners. Also, physicians and medical practitioners make use of hand-held illumination devices that have magnification including otoscopes, ophthalmoscopes and dermatoscopes. Typical otoscopes, ophthalmoscopes and dermatoscopes include a single lens for magnification and are designed for particular types of examination. However, a device that uses two magnification viewing lenses each having different powered magnification is described in U.S. Pat. No. 10,441,379, issued on Oct. 15, 2019 to Mullani entitled Multipurpose Medical Illuminator with Magnification, the substance of which is wholly incorporated herein by reference.

Hand-held dermoscopy devices that use light with magnification can utilize polarizers or liquid-glass interfaces to reduce surface reflection and aid in viewing of deeper structures in the skin. For example, the DermLite® Platinum® product, manufactured by 3Gen, LLC, was developed to provide variable polarization. Variable polarization is achieved by a rotating dial. Rotation of the polarizer to a cross-polarization orientation cancels out the surface reflection for an in-depth look at the deeper pigmentation in lesion structure. Rotation to a parallel polarization orientation allows a clear view of the skin surface. The DermLite® Platinum® product requires manual manipulation of the dial which may cause the user to lose the viewing spot, or otherwise interfere with examination. Further, DermLite® Platinum® does not provide a user the ability to view the skin with an instantaneous switch over from cross-polarization to parallel polarization. U.S. Pat. No. 5,742,392 issued on Apr. 21, 1998 to Anderson entitled Polarized Material Inspection Apparatus the entire substance of which is incorporated herein by reference also discusses a rotatable polarizer to capture intermediate polarizations mechanically.

Additional dermoscopy apparatuses that employ light polarization to aid in viewing human skin surfaces and deeper tissue and structures of the skin are known and described in U.S. Pat. No. 7,006,223, issued on Feb. 28, 2006 to Mullani, and U.S. Pat. No. 7,167,243, issued Jan. 23, 2007 to Mullani both entitled Dermoscopy Epiluminescence Device Employing Cross and Parallel Polarization, the substance of each of which is wholly incorporated herein by reference. While the apparatuses described in these patents allow for an instantaneous switch over from cross-polarization to parallel polarization by digital control, they do not present any solutions for extending such digital control to allow for the intermediate polarizations that are possible with the manual dial of the DermLite® Platinum® product. A dermoscopy device identified as the Dermlite® DL3 device is manufactured and marketed by 3Gen, Inc. of San Juan Capistrano, Calif. which uses light and polarization. In the Dermlite® DL3 hand-held device, a series of light emitting diodes ("LEDs") are concentrically positioned around a magnifying lens to assist in lighting of a magnified image. The device includes LEDs that provide reduced glare and cross-polarized light to aid in canceling the reflected light from the skin, and other LEDs on the device provide non-polarized light for traditional immersion fluid dermoscopy or for simply employing non-polarized light.

It is also well known that different colored light penetrates to different depths in human skin tissue. Specific color wavelengths are absorbed differently by different components of the skin tissue. Such use of colored LEDs in a dermatoscope is described in U.S. Pat. No. 7,027,153, issued on Apr. 11, 2006 to Mullani, and U.S. Pat. No. 7,167,244, issued on Jan. 23, 2007 to Mullani, both entitled Dermoscopy Epiluminescence Device Employing Multiple Color Illumination Sources, the substance of each of which is wholly incorporated herein by reference. The previously identified references disclose the combined use of white LEDs, UV/blue LEDs (405 nm), green/yellow LEDs (565 nm) and orange/red (630 nm). Alternatively, the U.S. Pat. Nos. 7,027,153 and 7,167,244 references suggest the use of LEDs with 480 nm, 580 nm and 660 nm wavelengths. In addition, a dermoscopy device identified as the Dermlite® II Multispectral dermoscopy device manufactured and marketed by 3Gen, Inc. of San Juan Capistrano, Calif. provides four sets of LED's comprising white, blue light (470 nm) for surface pigmentation, yellow light (580 nm) for superficial vascularity viewing, and red light (660 nm) for viewing of pigmentation and vascularity with the deeper-penetrating red light frequency.

Dermotoscopes using coloured LEDs to augment the viewing of pigmentation of human tissue including skin are shown and described in U.S. Pat. No. 9,458,990, issued Oct. 4, 2016 to Mullani entitled Dermoscopy Illumination Device With Selective Polarization And Orange Light For Enhanced Viewing of Pigmented Tissue, the substance of which is wholly incorporated herein by reference. In addition, a dermoscopy device identified as the Dermlite® DL4 dermoscopy device manufactured and marketed by 3Gen, Inc. of San Juan Capistrano, Calif. provides combinations of white LED lights and orange LED lights in both polarized and non-polarized combinations to provide enhanced viewing of skin pigmentation.

Furthermore, hand-held medical illuminators have been used to introduce light into human tissue for observing sub-dermal structures using side-transillumination techniques whereby the light source is caused to be in direct contact with the skin to transfer light directly into the skin. One such technique is known and taught in U.S. Pat. No. 5,146,923, issued on Sep. 15, 1992 to Dhawan entitled Apparatus And Method For Skin Lesion Examination, the substance of which is wholly incorporated herein by reference. A combination of a surface illumination, epiluminescence and transillumination apparatus and method is demonstrated in the Nevoscope™ product manufactured by Translite LLC of Sugar Land, Tex. Another known apparatus and method of viewing vein structures beneath the skin employs the use of transillumination as described in U.S. Pat. No. 7,874,698, issued on Jan. 25, 2011 to Mullani entitled Translumination Having Orange Color Light, the substance of which is wholly incorporated herein by reference. U.S. Pat. No. 7,874,698 describes the use of orange light between 580 and 620 nm for transillumination imaging of deeper blood vessels in skin tissue.

When employing light polarization to aid in viewing deeper structures of the skin, it would be desirable to allow for a wide range of selection by the user while avoiding cumbersome and error-prone manual controls. In addition when employing light polarization, it would be desirable to achieve incremental changes in the polarization without the requirement of mechanically rotating a polarizers over a wide range of polarization selection.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

BRIEF SUMMARY

The present disclosure contemplates various devices for overcoming the above drawbacks accompanying the known art. One aspect of the embodiments of the present disclosure is an illumination device for illuminating organic tissue such as a patient's skin. The illumination device may include a first set of one or more light emitting diodes (LEDs), a first polarizer arranged to polarize light emitted from the first set of one or more LEDs in a first polarization direction or first polarization state, a second set of one or more LEDs, a second polarizer arranged to polarize light emitted from the second set of one or more LEDs in a second polarization direction or second polarization state, a lens arranged to collect light from organic tissue illuminated by either one or both of the first and second sets of one or more LEDs, a viewing polarizer arranged to polarize the light collected from the organic tissue in the second polarization direction or second polarization state, a pulse generator operable to generate a pulsed voltage having an adjustable pulse width, and one or more drivers for driving one of the first and second sets of one or more LEDs according to the pulsed voltage and driving the other of the first and second sets of one or more LEDs according to an inverse of the pulsed voltage.

A further embodiment of the disclosed device relates to is an illumination device for illuminating organic tissue such as a patient's skin. The illumination device may include a first set of one or more light emitting diodes (LEDs), a first polarizer arranged to polarize light emitted from the first set of one or more LEDs in a first polarization direction or first polarization state, a second set of one or more LEDs, a second polarizer arranged to polarize light emitted from the second set of one or more LEDs in a second polarization direction or second polarization state, a lens arranged to collect light from organic tissue illuminated by either one or both of the first and second sets of one or more LEDs, a viewing polarizer arranged to polarize the light collected from the organic tissue in the second polarization direction or second polarization state. A microprocessor for receiving a user input signal to drive one or more drivers for driving one of the first and second sets of one or more LEDs according to a predetermined ratio for setting the light intensity of the first and second sets of LEDs to achieve variable polarization without the need to mechanically rotate a polarizer. A dial is provided to adjust the light intensity, wherein the movement of the dial is detected by an optical encoder and the optical encoder transmits a signal related to the detected movement of the dial to a microprocessor to determine the light intensity for the first and second sets of one or more LEDs.

Further benefits and advantages of the disclosed device will become apparent after careful reading of the detailed description with appropriate reference to the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 16 is a plan view of a LED printed circuit board assembly of the device according to the further embodiment prior to forming the assembly into the LED ring printed circuit board assembly;

FIG. 17 is a side perspective view of the LED ring printed circuit board assembly of the device according to the further embodiment;

FIG. 22 is a cut away bottom perspective view of the dial printed circuit board positioned relative to the rotating dial;

FIG. 23 is a cut away top perspective view of the dial printed circuit board positioned relative to the rotating dial;

FIG. 24 is a side view of dial printed circuit board positioned relative to the rotating dial;

FIG. 25 is a bottom view of the LED ring assembly junction with the main printed circuit board assembly.

DETAILED DESCRIPTION

Figure 1:
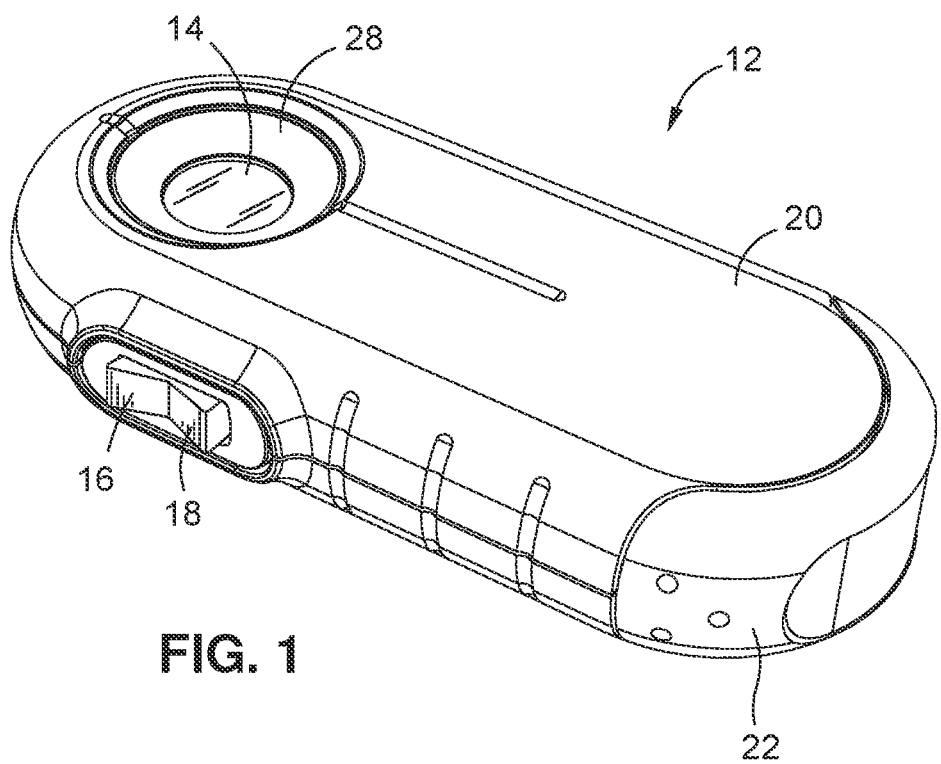
FIG. 1 is a top perspective view of the device according to a first embodiment of the present disclosure.

The present disclosure encompasses various devices for illuminating organic tissue such as a person's skin. The detailed description set forth below in connection with the appended drawings is intended as a description of several currently contemplated embodiments. It is not intended to represent the only form in which the disclosed subject matter may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

The background, summary and the description herein includes information that may be useful in understanding the present disclosure. It is not an admission that any of the information provided herein is prior art or relevant to the presently claimed inventive subject matter, or that any publication specifically or implicitly referenced is prior art.

In some embodiments, the numbers expressing dimensions, quantities, quantiles of ingredients, properties of materials, and so forth, used to describe and claim certain embodiments of the disclosure are to be understood as being modified in some instances by the term "about." Accordingly, in some embodiments, the numerical parameters set forth in the written description and attached claims are approximations that can vary depending upon the desired properties sought to be obtained by a particular embodiment.

In some embodiments, the numerical parameters should be construed in light of the number of reported significant digits and by applying ordinary rounding techniques. Notwithstanding that the numerical ranges and parameters setting forth the broad scope of some embodiments of the disclosure are approximations, the numerical values set forth in the specific examples are reported as precisely as practicable. The numerical values presented in some embodiments of the disclose may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the disclosure and does not pose a limitation on the scope of the claimed inventive subject matter. No language in the specification should be construed as indicating any non-claimed element essential to the practice of the inventive subject matter.

Groupings of alternative elements or embodiments of the inventive subject matter disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed. Various objects, features, aspects and advantages of the inventive subject matter will become more apparent from the following detailed description of preferred embodiments, along with the accompanying drawing figures in which like numerals represent like components.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

It should be noted that any language herein directed to a computer or computing devices should be read to include any suitable combination of computing devices, including servers, interfaces, systems, databases, agents, peers, engines, controllers, modules, or other types of computing devices operating individually or collectively. One should appreciate the computing devices comprise at least one processor configured to execute a computer program product comprising software instructions stored on a tangible, non-transitory computer readable storage medium (e.g., hard drive, FPGA, PLA, solid state drive, RAM, flash, ROM, etc.). The software instructions configure or program the computing device to provide the roles, responsibilities, or other functionality as discussed with respect to the disclosed devices. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In some embodiments, the various servers, systems, databases, or interfaces exchange data using standardized protocols or algorithms, possibly based on HTTP, HTTPS, TCP/IP, UPD/IP, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory. It is understood that the use of "configured to" or "programmed to" (or similar language) should not be construed to invoke interpretation under 35 USC 112(f).

Figure 2:
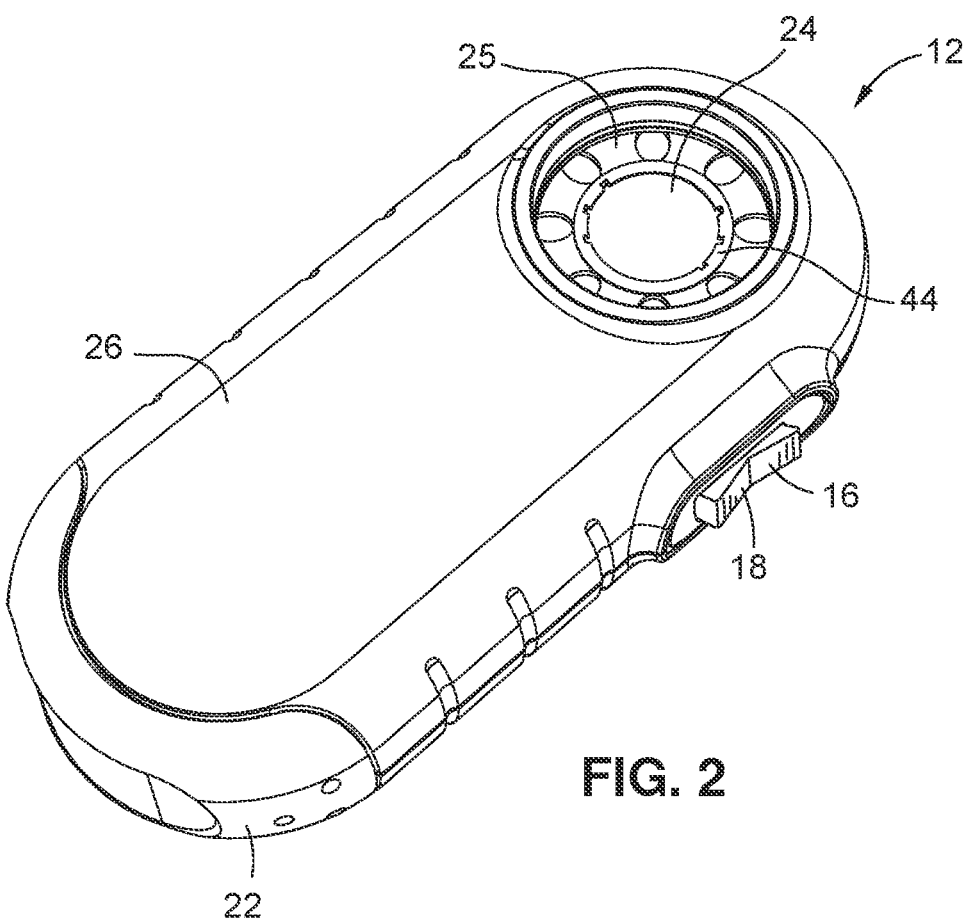
FIG. 2 is a bottom perspective view of the device according a first embodiment.

Referring particularly to FIGS. 1 and 2, there are shown top and bottom perspective views, respectively, of a dermoscopy epiluminescence device 12 according to an embodiment of the present disclosure. The device 12 may be lightweight and compact and may be sized to easily fit within the shirt pocket of a user. FIG. 1 shows the top perspective view of the device 12 showing the viewing port of an optical lens 14 incorporated into a housing 20. A battery cover 22 may be removably secured to the housing 20 to provide access to an interior compartment for insertion and removal of a battery. As shown in FIG. 2, a light portal may be incorporated into the housing 20 to expose a viewing polarizer 24. A plurality of light emitting diodes (see FIGS. 3 and 4) may encircle the viewing polarizer within the housing 20 and direct light though a multiple layer filter ring 25 in order to selectively illuminate the surface of the organic tissue with cross-polarized and parallel-polarized light. By operation of switches 16, 18, a user of the device 12 can control the relative portion of cross-polarized light and parallel-polarized light by pulse width modulation, thus selectively increasing and decreasing the effective penetration depth of the view. For example, a switch 16 for increasing the effective penetration depth and a switch 18 for decreasing the effective penetration depth may be provided as momentary up and momentary down positions of a usually neutral rocker switch as shown. Alternatively, the switches 16, 18 may be individual push buttons, touchscreen elements, opposing inputs of a slider, dial, or knob, etc.

Figure 3:
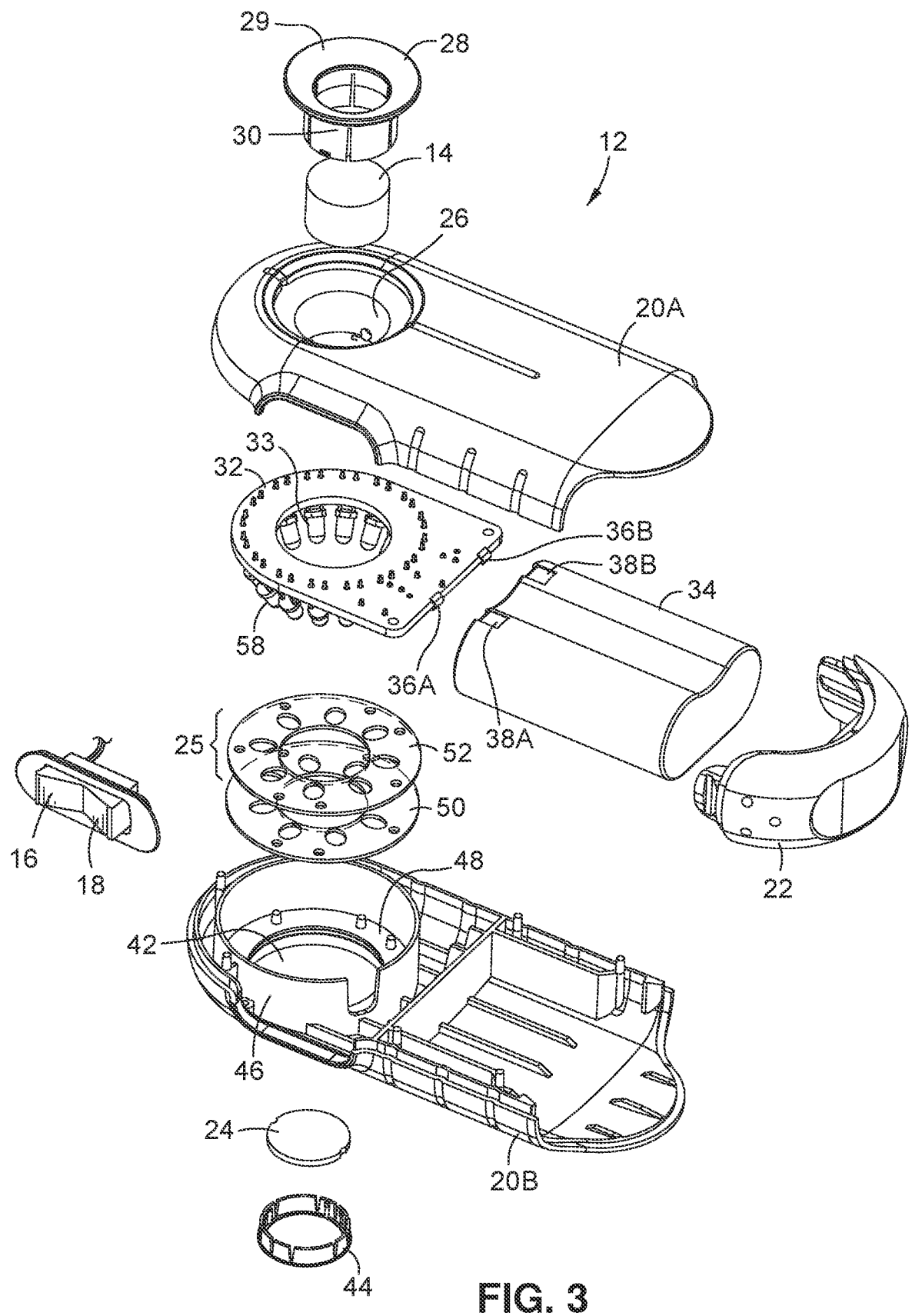
FIG. 3 is an exploded top view of the device according to the first embodiment.
Figure 4:
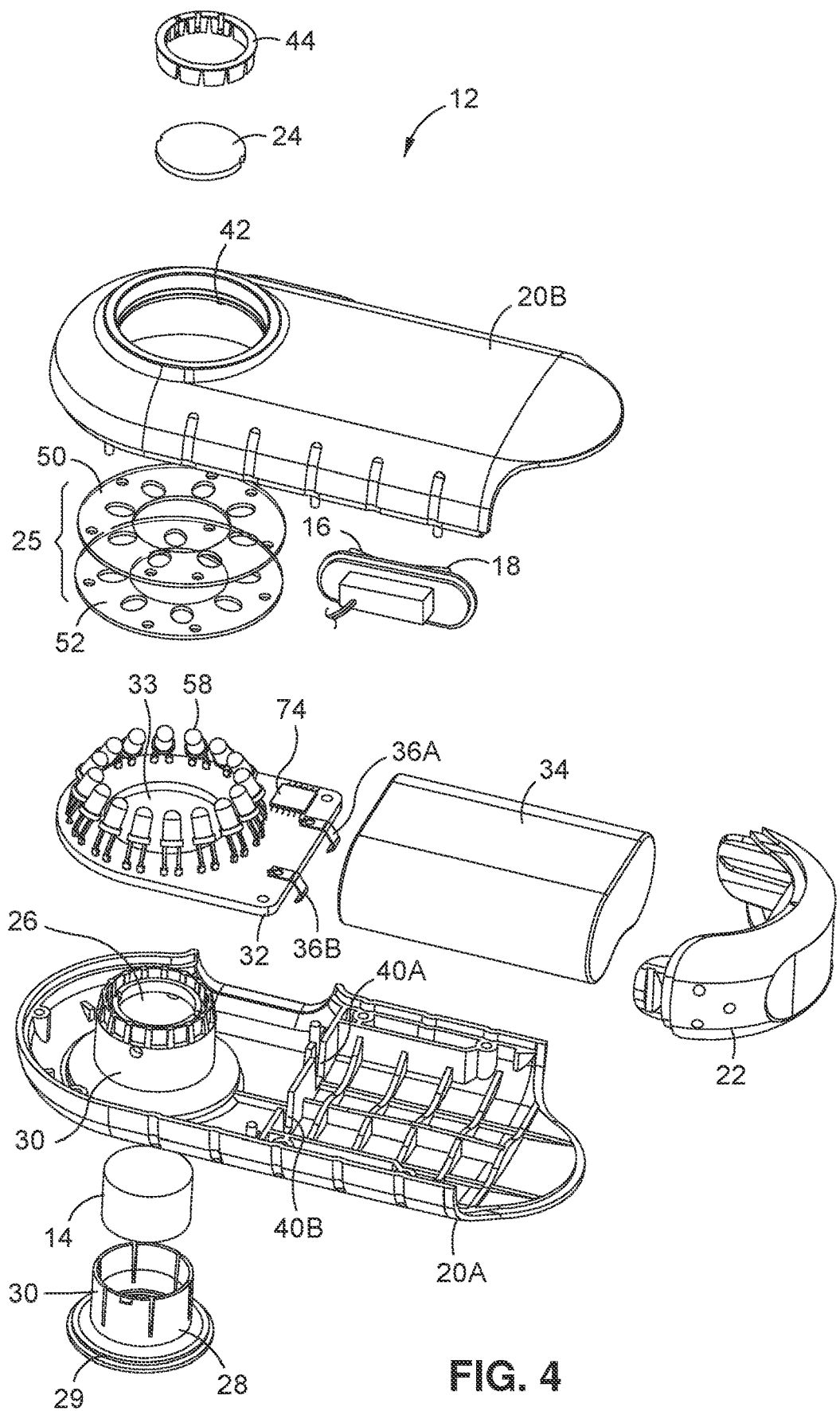
FIG. 4 is an exploded bottom view of the device according to the first embodiment.

FIG. 3 is an exploded top view of the device 12 and FIG. 4 is an exploded bottom view of the device 12. The housing 20 may include a top component 20a and bottom component 20b. The top component 20a, bottom component 20b, and battery cover 22 may be formed from molded lightweight durable plastic. The plastic may be a PVC derivative material and may be formed from acrylic or lexan. Additionally, the housing may be formed from metal such as aluminum. Components 20a, 20b and cover 22 may be interconnected to form the outer housing 20 as shown in FIGS. 1 and 2.

The top housing component 20a may include an aperture 26 for receiving the combination of the optical lens 14 inserted within a lens sleeve 28. Shown best in FIG. 4, the underside of the top housing component 20a is shown wherein the aperture 26 incorporates a downwardly protruding (upwardly in FIG. 4) collar 30 for receiving the lens 14 within the lens sleeve 28. The lens sleeve 28 may incorporate an annular lip 29 which engages sloped sides of the aperture 26 to complete the exterior of the viewing port of the housing 20. The lens sleeve 28 may operate to securely hold the lens 14 in place within the aperture 26. The lens 14 is preferably a 15 mm diameter Hastings lens with a 10× optical gain. Alternatively, the lens may be a single convex lens, a combination of two or more lenses, a double achromat lens, or a combination of double achromat lenses. In addition, the lens may incorporate aspherical lenses to accommodate better optics and lower distortion. Lenses coated with an antireflection coating may be used and a color filter may additionally be included to selectively filter light passing through the lens.

Although the drawings show a hand-held unit without imaging equipment attached, it is contemplated by the present disclosure that the same could be used with a camera, and that the size and shape of the lens could be modified to accommodate the same.

The protruding collar 30 may be part of the unitary structure of the upper housing component 20a. The collar 30, which may be cylindrical, may protrude through the interior components of the housing 20, including a printed circuit board (PCB) 32 having an opening 33, to extend to the light portal of the bottom component 20b. A battery 34 may nest within a battery chamber formed by the top component 20a and bottom component 20b. The PCB 32 may include electrical contacts 36a and 36b for interfacing with battery contacts 38a and 38b. The upper housing 20a may include slots 40a and 40b to allow the PCB contacts 36a and 36b to protrude from the circuit board 32 into the battery chamber and contact the battery leads 38a and 38b. The battery 34 may be an extended charge lithium battery. However, it is understood and contemplated by the present disclosure that the battery could be any suitable battery package such as a one-time lithium battery or rechargeable lithium battery. The disclosure additionally contemplates use of a DC power supply or an external power supply through a wire through contacts or a power port such as a USB or USB-C port.

The bottom component 20b may include a viewing aperture 42 aligned with the aperture 26 of the top component 20a. At the viewing aperture 42, the viewing polarizer 24 inserted within a sleeve 44 may cap off the opening of the collar 30. The viewing polarizer 24 may be composed of acrylic plastic with polarization material embedded within the polarizer. It is contemplated that the viewing polarizer 24 may alternatively be constructed of glass, with polarization material embedded or coated on the glass. In addition, the viewing polarizer 24 may be coated with a filter material that can selectively filter out some of the light frequencies emanating from the object. Alternatively, a secondary filter assembly made of plastic or glass with the capability of filtering the light may be placed in the path of the viewing lens 14 to filter out some of the light.

The bottom housing component 20b may include a bottom collar 46 formed therein. A lip 48 incorporating a plurality of guide tabs may be formed between the collar 46 and the viewing aperture 42. The lip 48 and guide tabs may be adapted to engage a bottom annular polarizer 50 and a top annular polarizer 52. The top 52 and bottom 50 polarizers may have different polarization directions and may, for example, be 90 degrees out of phase. The bottom 50 polarizer may be in cross polarization with the viewing polarizer 24, and the top polarizer 52 may be in parallel polarization with the viewing polarizer 24. The top 52 and bottom 50 polarizers may be composed of acrylic plastic and may include polarization at different angles. The polarizers 50 and 52 may also be coated with a special material to filter out some of the light emanating from the LEDs, or alternatively the annular polarizer 50 and 52 may be sandwiched with a color filter acrylic material. The viewing aperture 42 may be wide enough to permit a viewing corridor from the lens sleeve 28 through the housing 20 to the viewing aperture 42 while allowing portions of the top 52 and bottom 50 polarizers to be exposed and to filter light emitting diodes inside the housing 20.

In the example shown in the drawings, sixteen light emitting diodes 58 ring the circuit board 32, though it is contemplated that the number of diodes may be greater or less. The diodes 58 are preferably white high light output Indium Gallium Nitride LEDs, but any suitable lighting diodes are appropriate. Every other diode 58 may be on the same circuit, for example, the even diodes may be on a single circuit and the odd diodes may be on a separate single circuit. In the shown embodiment, the LEDs 58 are a standard white LED made with phosphorescence phosphors to create white light. It is additionally contemplated by the present disclosure that tri-colored LEDs, with individual red, green and blue LEDs that can combine to form white light, may be utilized. It is contemplated by the present disclosure that the LEDs may have focusing lenses to concentrate the light into a smaller and tighter beam. The LEDs may additionally be comprised of indium gallium arsenide material, or any other like semiconductor material.

As shown in FIG. 4, the PCB 32 may additionally incorporate an integrated circuit 74 for selectively driving the LEDs 58. The integrated circuit 74 may be electrically connected to the switches 16, 18 and the battery 34 via the PCB 32. The integrated circuit 74 may additionally be communicatively coupled to an external device (e.g. a smartphone or other mobile device) via radio frequency transmission according to any of various wireless communication protocols such as Bluetooth. By manually operating the switches 16, 18 and/or wirelessly communicating with the integrated circuit 74 from an external device, a user may selectively drive the LEDs 58 as described in more detail below in order to increase or decrease the effective penetration depth when viewing organic tissue using the device 12.

The first polarizer filter 50 may comprise a planar annular ring defining a generally circular center opening and an outer ring. The center opening of the annular ring of the first polarizer 50 may be positioned in alignment with the circular optical lens 14 to provide an unobstructed view of the organic tissue through the lens 14 and the housing 20. The outer ring of the first polarizer 50 may be arranged to polarize light emitted from a first set of one or more LEDs 58 (e.g. the even diodes) in a first polarization direction and to include a plurality of openings sized and positioned to correspond to the diodes 58 of a second set of one or more LEDs 58 (e.g. the odd diodes). Thus, the light emitted from the second set of one or more LEDs 58 may pass through the openings unfiltered by the first polarizer 50. The second polarizer filter 52 may likewise comprise a planar annular ring defining a generally circular center opening and an outer ring, with the center opening of said annular ring of the second polarizer 52 positioned in alignment with the circular optical lens 14 to provide an unobstructed view of the organic tissue through the lens 14 and housing 20. The second polarizer 52 may be 90 degrees out of phase with the first polarizer 50 as noted above. The outer ring of the second polarizer 52 may be arranged to polarize light emitted from the second set of one or more LEDs 58 (e.g. the odd diodes) in a second polarization direction. Like the first polarizer 50, the second polarizer 52 may have a plurality of openings, but in the case of the second polarizer 52 the plurality of openings may be sized and positioned to correspond to the diodes 58 of the first set of one or more LEDs 58 (e.g. the even diodes). Thus, the light emitted from the first set of one or more LEDs 58 may pass through the openings unfiltered by the second polarizer 52.

Figure 5:
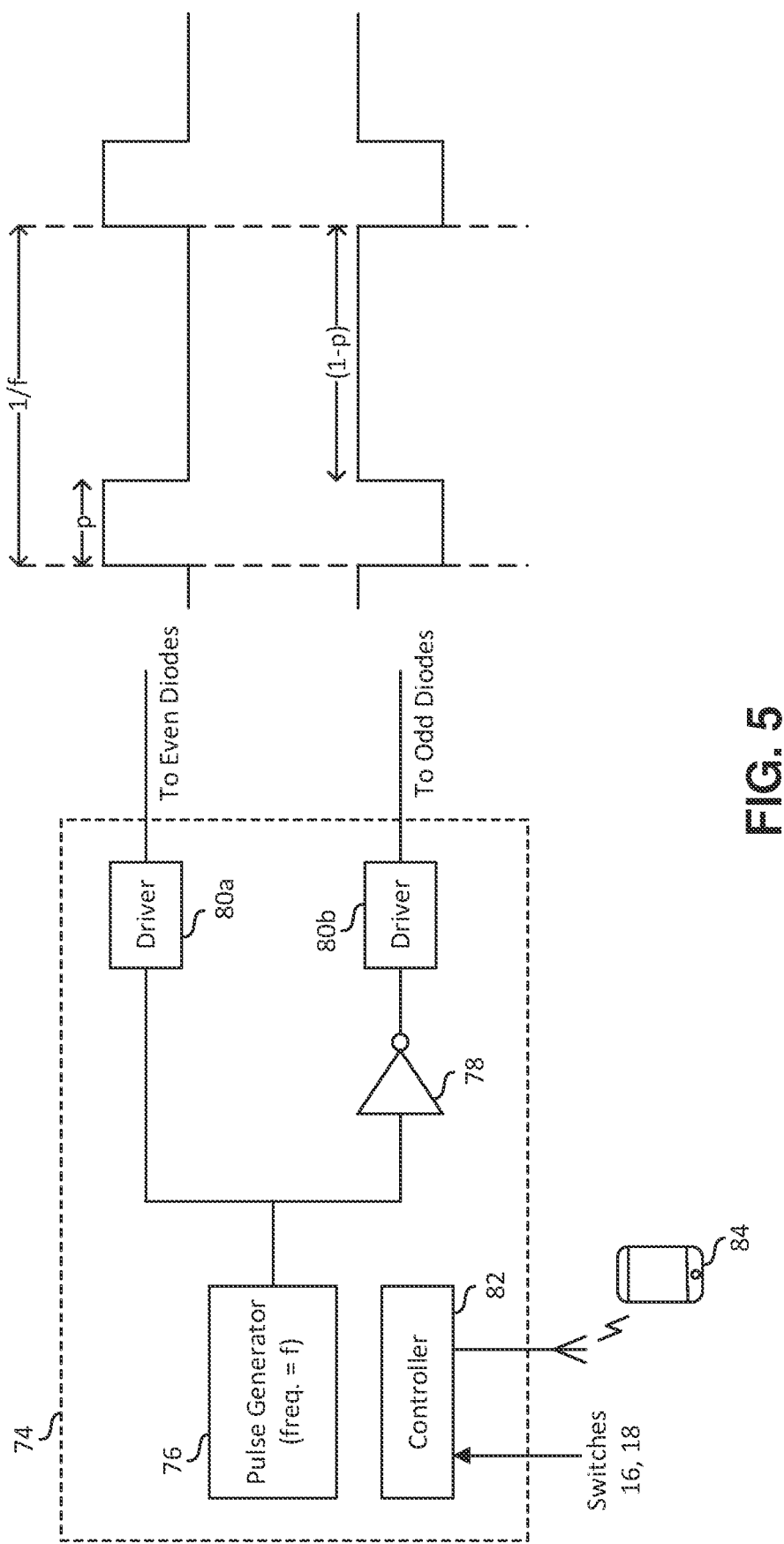
FIG. 5 is a schematic view of the device showing circuit components for operating the device according the first embodiment.

FIG. 5 is a schematic view of the device 12 showing circuit components for operating the device 12. By way of example, the components shown in FIG. 5 are depicted as being components of the integrated circuit 74 (see FIG. 4), which may be a microcontroller for example. However, this is only one example, and it is contemplated that the functionality of the illustrated circuit components may be implemented on the PCB 32 in other ways as well, e.g. divided between multiple integrated circuits. As shown, the device 12 may include a pulse generator 76, an inverter 78, a first driver 80a, a second driver 80b, and a controller 82.

The pulse generator 76 may be operable to generate a pulsed voltage having an adjustable pulse width p for driving one or both of the first and second sets of LEDs 58 at a frequency f. In response to the pulsed voltage output by the pulse generator 76, the first driver 80a may drive the first set of one or more LEDs 58 (e.g. the even diodes). Thus, as shown on the right-hand side of FIG. 5, the pulse of width p may represent a portion of a period 1/f during which the even diodes are turned on, such that reducing the pulse width p causes the even diodes to dim as perceived by the human eye or by a camera with a frame rate or shutter speed less than the frequency f. Meanwhile, in response to the inverted pulsed voltage as output by the inverter 78, the second driver 80b may drive the second set of one or more LEDs 58 (e.g. the odd diodes). Thus, as shown on the right-hand side of FIG. 5, the inverse pulse width (1-p) may represent a portion of a period 1/f during which the odd diodes are turned on, such that reducing the pulse width p causes the odd diodes to brighten as the even diodes dim. By such an arrangement, the same total power may be used to drive the LEDs 58 irrespective of the pulse width p, with the even and odd diodes 58 being oppositely brightened and dimmed according to the setting of the pulse width p.

Operation of the pulse generator 76 may be controlled by the controller 82 in response to user inputs made using the switches 16, 18 (see FIG. 1 etc.). For example, as explained above, the switch 16 may increase the effective penetration depth when viewing organic tissue using the device 12 and the switch 18 may decrease the effective penetration depth. To this end, the controller 82 may increase the pulse width p in response to a user pressing the switch 16 and may decrease the pulse width p in response to a user pressing the switch 18. When the pulse width p is increased, the first set of one or more LEDs 58 (e.g. the even diodes), which are polarized in the first polarization direction by the first polarizer 50, are driven for a greater portion of each cycle 1/f. With the viewing polarizer 24 being cross polarized relative to the first polarization direction, the reflected light of the first LEDs 58 off the outermost layers of the organic tissue is blocked by the viewing polarizer 24. Meanwhile, the reflected light of the first LEDs 58 from deeper layers of the organic tissue will have a shifted polarization due to refraction and will thus be at least partially transmitted by the viewing polarizer 24. As a result, driving the first set of LEDs 58 (e.g. the even diodes) for a greater portion of each cycle may have the effect of increasing the effective penetration depth when viewing the organic tissue, thus deemphasizing surface features.

The opposite is true of the second set of LEDs 58 (e.g. the odd diodes), which are polarized in the second polarization direction by the second polarizer 52. With the viewing polarizer 24 sharing the second polarization direction of the light of the second LEDs 58, the reflected light of the first LEDs 58 off the outermost layers of the organic tissue is polarized parallel to the viewing polarizer 24 and thus transmitted. Meanwhile, the reflected light of the first LEDs 58 from deeper layers of the organic tissue will have a shifted polarization due to refraction and will thus be at least partially blocked by the viewing polarizer 24. As a result, driving the second set of LEDs 58 (e.g. the odd diodes) for a greater portion of each cycle may have the effect of decreasing the effective penetration depth when viewing the organic tissue, thus emphasizing surface features.

In response to the user pressing the switches 16, 18, the controller 82 may increase or decrease the pulse width p by set increments, for example, p=0%, p=20%, p=40%, p=60%, p=80%, and p=100%, where percentages refer to one cycle 1/f. When the switch 16 is pressed repeatedly until the pulse width p is set to 0%, the first set of LEDs 58 (even diodes) are off for the entire cycle while the second set of LEDs 58 (odd diodes) are on, resulting in parallel polarization of surface reflections and a minimum effective penetration depth. Conversely, when the switch 18 is pressed repeatedly until the pulse width p is set to 100%, the first set of LEDs 58 (even diodes) are on for the entire cycle while the second set of LEDs 58 (odd diodes) are off, resulting in cross polarization of surface reflections and a maximum effective penetration depth. In between these two extremes, a portion of the light will be cross-polarized with the remainder parallel-polarized, resulting in an intermediate effective penetration depth according to the user's incremental selection. The relative portion of the light that is cross-polarized and parallel-polarized may be as shown in the following table.

TABLE 1

| Pulse Width "p" | Cross-Polarized Portion | Parallel-Polarized Portion |
| --- | --- | --- |
| 0% | 0% | 100% |
| 20% | 20% | 80% |
| 40% | 40% | 60% |
| 60% | 60% | 40% |
| 80% | 80% | 20% |
| 100% | 100% | 0% |

Larger increments (e.g. p=0%, p=25%, p=50%, p=75%, and p=100%) and smaller increments (e.g. p=0%, p=10%, p=20%, p=30%, p=40%, p=50%, p=60%, p=70%, p=80%, p=90%, and p=100%) are also contemplated, as well as a continuous or substantially continuous control, allowing the user to smoothly transition the view in the depth direction of the organic tissue.

As shown in FIG. 5, user inputs to the controller 82 may alternatively or additionally be made using an external device 84 (e.g. a smartphone or other mobile device) via wireless communication (e.g. Bluetooth). It is contemplated, for example, that the external device 84 may run a mobile application (e.g. a downloadable "app") that establishes a wireless connection with the controller 82 and generates a graphical user interface for adjusting settings of the pulse generator 76. Such a graphical user interface may include, for example, virtual sliders, buttons, etc. having the functions of the switches 16, 18 shown in FIG. 1 for controlling the pulse width p. Additional functionality of the graphical user interface (or of additional switches on the device 12) may include, for example, adjusting the frequency f of the pulsed voltage (e.g. from 100 to 10,000,000 Hz), adjusting the forward current of the LED (e.g. by controlling the drivers 80a, 80b) to allow analog control of the intensity of light, changing the mode of operation of the device 12 (e.g. to turn off the pulse generator 76 entirely and allow for static operation of the first and/or second sets of LEDs 58), and/or communicating with a camera of the external device 84 to capture an image of the organic tissue. In this regard, it is contemplated that the device 12 may be attachable to the external device 84 (e.g. by magnets and/or threaded connection) to align a camera of the external device 84 with the optical lens 14 of the device 12. With the aid of a camera, it is contemplated that a three-dimensional map of the organic tissue may be constructed by combining images taken at a plurality of effective penetration depths.

In the illustrated example described above, it is assumed that every other LED 58 is on the same circuit, with the even diodes on one circuit and the odd diodes on another circuit. That is, the LEDs 58 are grouped into two sets, each corresponding to its own polarizer 50, 52. However, the disclosure is not intended to be so limited, and greater numbers of sets of LEDs 58 are contemplated as well. For example, a third set of LEDs 58 may be provided that emit light that is neither polarized by the bottom polarizer 50 nor by the top polarizer 52 and instead remains non-polarized (e.g. by passing through corresponding holes in both polarizers 50, 52). Upon reflection at the organic tissue, such non-polarized light may be transmitted/blocked by the viewing polarizer 24 to a degree that does not depend on the reflection depth. A fourth set of LEDs 58 may be provided that similarly emit non-polarized light but at an ultraviolet wavelength or another wavelength (e.g. blue). The LEDs 58 may be arranged in a single ring such that one out of every four LEDs 58 is on the same circuit. In the case of such three-circuit and four-circuit designs, it is contemplated that the first and second sets of LEDs 58 may be driven in response to the output of the pulse generator 76 as shown in FIG. 5, with the third and fourth sets of LEDs 58 being independently controlled by the controller 82 in response to user input (e.g. mode settings selected by an external device 84 or by additional switches on the device 12).

Along the same lines, sets of LEDs 58 are shown as each having the same number of LEDs. However, the disclosure is not intended to be limited in this regard. For example, the first set of LEDs 58 may have fewer LEDs than the second set of LEDs 58, with the power level for the first set being greater to compensate for the reduced number of LEDs (e.g. by appropriate control of the drivers 80*a*, 80*b*). The same is true in the case of three, four, or any number of sets of LEDs 58, with the respective power levels being modified independently to account for differences in the number of LEDs of each circuit (as well as differences in the desired intensity of light). As noted above, independently modifying the power levels of the LEDs 58 (e.g. adjusting the forward current) may, in general, be used to control the intensity of light. Such analog control may be used instead of or in combination with the digital pulse width modulation described above in order to produce the desired combinations of cross-polarized and parallel-polarized light to change the effective penetration depth as described throughout this disclosure.

In the illustrated embodiments, the positions of various components of the device 12 (e.g. the polarizers 50, 52) are described in relation to the positions of LEDs 58. However, it is contemplated that the defined positions of the LEDs 58 more generally can be understood as the positions of functional light sources, which can be arbitrarily distant from the positions of actual LEDs, a light box, etc. through the use of fiber optics. For example, each of the LEDs 58 shown in the drawings may represent the output end of an optical fiber, with the input ends thereof receiving light from a shared illuminator.

It is known that combining orthogonally polarized light (parallel light combined with cross-polarized light) is effectively the same as unpolarized light. The polarization state of light can be mathematically described by the Stokes vector. The Stokes vector is determined by measuring the intensity of light through a parallel polarizer placed in front of a light sensor at several different orientations. Intensity measurements are also taken with a left hand and right hand circular polarizer in front of the light sensor. These intensity measurements are placed into a matrix where: $I_0$=the intensity of light filtered through a parallel polarizer at zero degrees; $I_{90}$ is the intensity of light filtered through a parallel polarizer at 90 degrees; and $I_{45}$ and $I_{135}$ is the detected intensity of the light filtered through the polarizer at 45 and 135 degrees, respectively. Regarding the Stokes parameters: $S_0$ is calculated from the sum of $I_0$ and $I_{90}$; $S_1$ is the difference between $I_0$ and $I_{90}$; $S_2$ is the difference between $I_{45}$ and $I_{135}$; and $S_3$ is the difference between intensity filtered through circular polarizers $I_{LHC}$ and $I_{RHC}$. The Stokes vector matrix is provided below.

$$S = \begin{bmatrix} S_0 \\ S_1 \\ S_2 \\ S_3 \end{bmatrix} = \begin{bmatrix} I_0 + I_{90} \\ I_0 - I_{90} \\ I_{45} - I_{135} \\ I_{LHC} - I_{RHC} \end{bmatrix},$$

For unpolarized light, the light waves are randomly polarized and the intensity of the unpolarized light as measured through a polarizer are the same no matter the polarizer orientation. As such, for unpolarized light $I_0 = I_{90} = I_{45} = I_{135}$.

Using the Stokes parameters, the results of the matrix describe the state of polarization for common polarization configurations:

$$\begin{bmatrix} 1 \\ 1 \\ 0 \\ 0 \end{bmatrix} \text{parallel or linearly polarized (horizontal);}$$

$$\begin{bmatrix} 1 \\ -1 \\ 0 \\ 0 \end{bmatrix} \text{parallel or linearly polarized (vertical)}$$

$$\begin{bmatrix} 1 \\ 0 \\ 1 \\ 0 \end{bmatrix} \text{parallel or linearly polarized(+45 degrees)}$$

$$\begin{bmatrix} 1 \\ 0 \\ -1 \\ 0 \end{bmatrix} \text{parallel or linearly polarized(-45 degrees)}$$

$$\begin{bmatrix} 1 \\ 0 \\ 0 \\ 1 \end{bmatrix} \text{right hand circular polarized}$$

$$\begin{bmatrix} 1 \\ 0 \\ 0 \\ -1 \end{bmatrix} \text{left hand circular polarized}$$

$$\begin{bmatrix} 1 \\ 0 \\ 0 \\ 0 \end{bmatrix} \text{unpolarized}$$

For Stokes parameters $S_1$, $I_0$ and $I_{90}$ cancel each other out and resolve to zero (0). For $S_2$, $I_{45}$ and $I_{135}$ cancel each other out and resolve to zero (0). For $S_3$, since the devices described herein do not use circular polarization also therefore resolves to zero (0). As such the configuration results in the following Stokes vector:

$$\begin{bmatrix} 1 \\ 0 \\ 0 \\ 0 \end{bmatrix} \text{unpolarized}$$

In the case of an equal combination of vertically polarized light and horizontally polarized light as described in the embodiments of the devices described herein, $I_0=I_{90}$, so for Stoke parameter $S_1$, $I_0$ and $I_{90}$ cancel out and resolve to zero (0). When the polarizer is diagonal $I_{45}=I_{135}$ (although half of the intensity of $I_0$ or $I_{90}$), so for $S_2$ $I_{45}$ and $I_{135}$ cancel out and resolve to zero (0). Again, there is no circular polarization so $S_3$ is zero (0). The end result of the Stoke vector is the non-polarized light:

$$\begin{bmatrix} 1 \\ 0 \\ 0 \\ 0 \end{bmatrix} \text{unpolarized}$$

The polarization as presented in the disclosed devices uses parallel polarization that provides a higher contrast image of the linear and cross polarized light, as opposed to elliptical polarization. With the disclosed device a healthcare practitioner can change the degrees of polarization to view the structural skin at differing depths to compare and contrast. Also, images that may be captured by a camera attached to the devices disclosed herein can store the images for later viewing and comparing and contrasting to aid in diagnosis and treatments.

Figure 6:
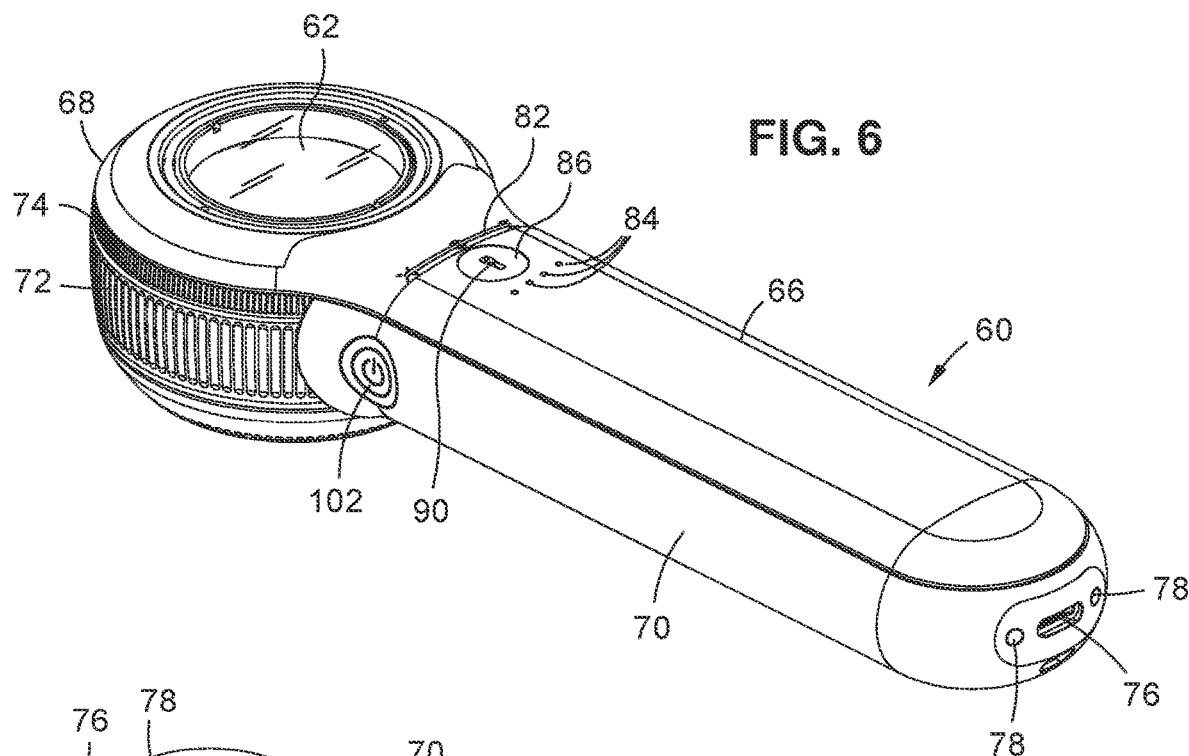
FIG. 6 is a top perspective view of the device according to the further embodiment.
Figure 7:
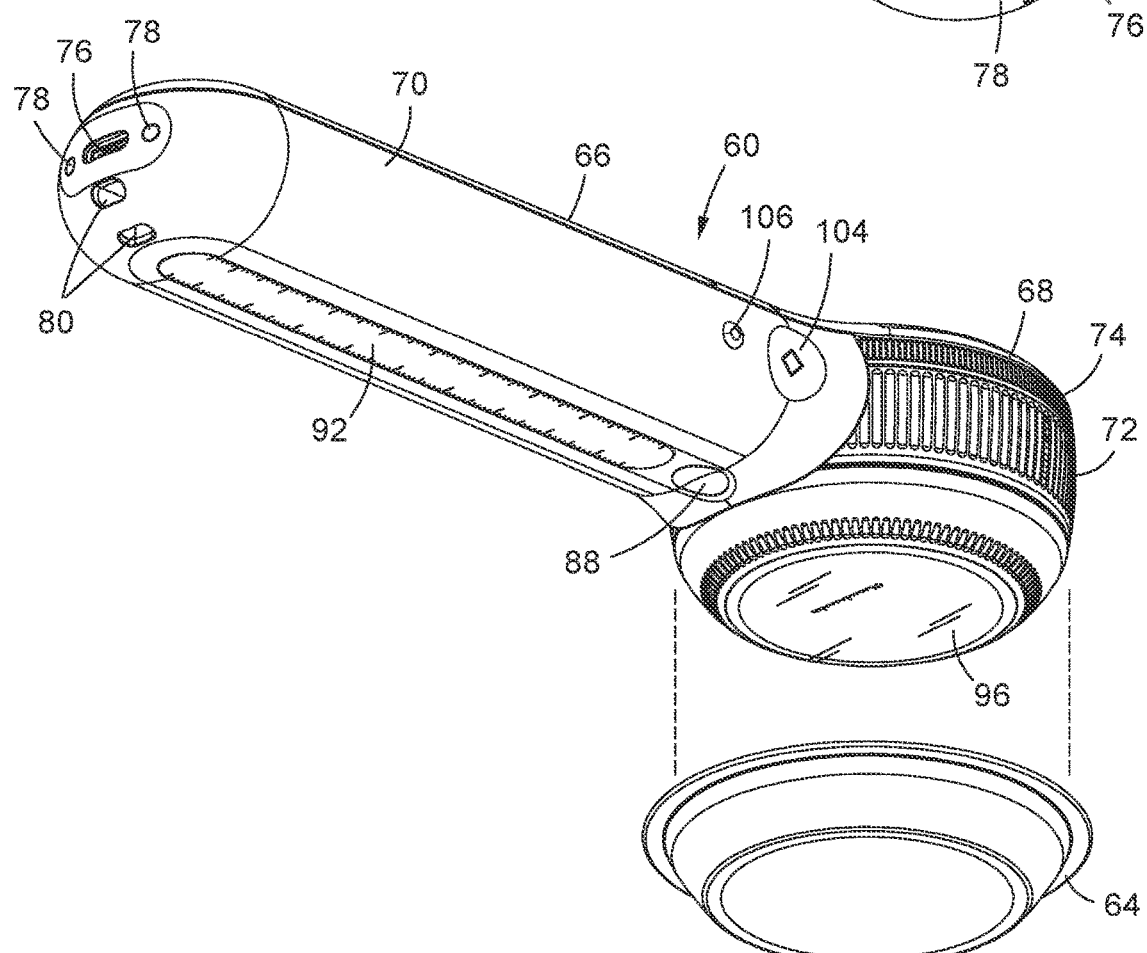
FIG. 7 is bottom perspective view of the device according to the further embodiment with a disposable sanitary transparent cap shown exploded from the device.
Figure 8:
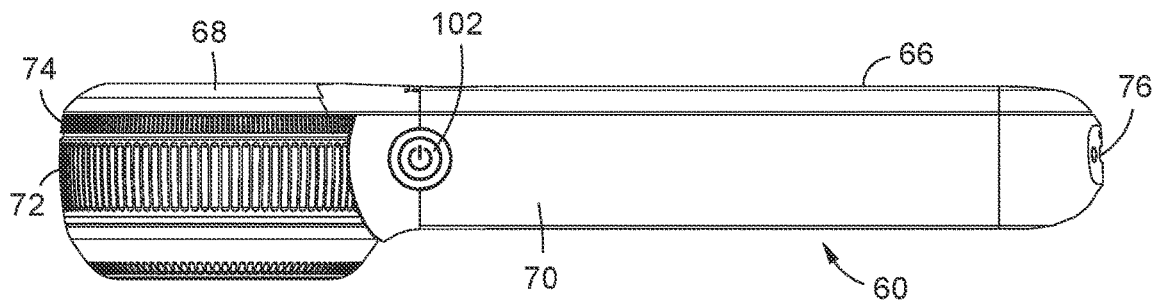
FIG. 8 is a left side view of the device according to the further embodiment.

Referring particularly to FIGS. 6-7 there is shown an illumination device 60 representing a further embodiment of the device described herein. FIG. 6 shows the distal (away from the organic material to be viewed) upper perspective view of the illumination device 60, the top side of the device from which a user would view through the magnification lens 62. FIG. 7 is a right-side lower perspective view of the device 60 showing the proximal (closest to the organic material to be viewed) of the illumination device 60. The proximal side is lower side of the device from which LEDs emit light to the object to be viewed. FIG. 7 also shows an auxiliary removably attachable disposable clear plastic cap 64 attachable to the device 60 housing 66. The disposable cap 64 may be applied to the device over the faceplate 96 and the surrounding surface of the housing 66 for sanitary reasons to assist in preventing cross-contamination when using the device 60 on patients. The plastic cap 64 is formed of a clear plastic material with flexion in the structure to allow it to be snap fit over the faceplate 96 and surrounding area, to be securely attached when in use and easily removed by hand after the cap 64 is to be discarded. The plastic of the cap 64 may assist in keeping pathogens from attaching to the device 60 by covering a portion of the proximal surface of device 60 and the cap 64 may be disposed of after a single use. Because the plastic of the cap 64 is transparent and has a low birefringence so that it does not disrupt the polarization state of the light passing through the cap 64 and does not significantly interfere with viewing the organic matter to be viewed through the device 60 optics including the lenses 62.

Referring to FIGS. 7-11 collectively, there are shown a number of external features of the device 60. The housing 66 includes a head portion 68 incorporating the device optics and the handle portion 70 incorporating electronic components of the device 60. In operation, a user grasps the handle portion 70 to hold the head 68 over an area of interest. The handle portion 70 has a number of LED indicators for showing the mode of operation or power, and positioned at the junction between the head portion 68 and the handle portion 70 a number ergonomically placed buttons are provided to allow a user to initiate various lighting modes and power the device.

The head portion 68 additionally incorporates two manual dials. A spacer dial 72 is provided to allow a user to manually rotate to extend a threaded spacer that extends and retracts from the head 68 (not shown in FIGS. 6-11, being retracted in such drawings). The spacer dial 72 is provided for adjusting position of a spacer by extending or retracting the same to adjust the focal distance to the object or tissue that is to be viewed (not shown). The spacer dial and spacer (not shown) operates similar to and consistent with the dial and spacer shown in U.S. Pat. No. 9,458,990, issued Oct. 4, 2016 to Mullani entitled Dermoscopy Illumination Device With Selective Polarization And Orange Light For Enhanced Viewing of Pigmented Tissue, the substance of which is wholly incorporated herein by reference. The head portion 68 additionally includes a polarization dial 74 that may be manually turned by a user in combination with other buttons to adjust or vary polarization in certain modes of operation, described in detail below.

A power port 76 is provided at the end of handle portion 70, which is a USB-C port, however, it is contemplated by this disclosure that the power port may be any suitable electrical connector. The power port 76 is adapted to receive a male power port plug to supply power to the device and to charge an on-board battery (not shown in FIGS. 6-11). In addition to the power port 76, contact pins 78 are also provided to provide separate means of powering the device and charging the battery. A complementary charging base (not shown) may be provided with contacts to provide charge to the device 60. The contact pins 78 and charging device (not shown) operate similar to and consistent with the charging base shown in U.S. Pat. No. 9,458,990, issued Oct. 4, 2016 to Mullani entitled Dermoscopy Illumination Device With Selective Polarization And Orange Light For Enhanced Viewing of Pigmented Tissue, the substance of which is wholly incorporated herein by reference. In addition, it is contemplated that an induction charging system for the on-board battery may be utilized. Also, lanyard openings 80 are provided for inserting a string, chord or other like device into the one of the openings 80 and through and out of another of the openings 80 to attach a chord, lanyard string or loop handle to the end of the handle 70.

Referring to the various external indicators on the device 60 in FIGS. 7-11, there is shown on the distal side of the device 60, polarization indicator bar 82. In operation when the device 60 is powered, the indicator 82 shows the degree of polarization. The light bar 82 with a first indicator LED light activated on the far left demonstrates cross polarization, and an "x" is imprinted on the housing 66 next to the first LED on the far left. The indicator LED light activated on the right side of the LED bar 82 indicates parallel polarization, with two parallel lines imprinted on the device. An indicator LED light activated in the center of LED bar 82 indicates 50% cross polarization and 50% parallel polarization resulting in non-polarized light. The light bar 82 can be activated along any point along the bar 82 to indicate the degree of polarization with cross polarization on the left side and parallel polarization on the right side as the extremes. Also located on the distal side of the handle 70 are four charge indicator LEDs 84 for providing a user with charge status of the battery (not shown). When all four indicators LEDs 84 are activated, this indicates a charge between 76 and 100 percent charge. Likewise, when three LEDs are activated, this indicates a charge between 51 and 75 percent. When two lighted LEDs 84 are indicated, the remaining charge is between 26 and 50 percent. Finally, when one of the LEDs 84 is activated, the remaining charge is between 1 and 25%. In addition, a pigment boost LED indicator 98 is activated when the device 60 is operated in pigment boost mode, where orange LEDs are activated. Also, an ultraviolet (UV) LED indicator 100 is activated when the device 60 is operated in UV mode.

Located on the distal side of the handle 70 is a torch button 86 is provided that activates and deactivates a flashlight, or torch light 86 on the proximal side of the handle 70. The torch light 88 provides convenient tool for use by the medical practitioner to operate much like a flashlight and is not associated with the optics or polarization filters of the device 60. Two indicator LEDs 90 are located in the center of the torch button 86 to identify status of the torch light 88. Tapping the torch button 86 activates the torch light 88, and in the instance where the LEDs in the device 60 head are turned on, those LED lights will turn off for operating in torch mode. In operation, the user may tap and hold the torch button 86 while simultaneously turning the polarization dial 74 to adjust the torch LED 88 brightness. The microprocessor (not shown in FIGS. 6-11) may store in an on board non-transitory memory device (not shown in FIGS. 6-11) the level of brightness, and upon the next initiation of the torch 86, the torch will light at the same brightness.

A power button 102 is provided on left side of the housing 66 of the device 60 to turn on the device 60 power. Upon tapping power button 102 the device defaults to cross polarizer mode, and as such the light bar 82 show the status of cross polarizing mode. The power button 102 can then be tapped to toggle between cross polarized mode and non-polarized mode (the indicator bar 82 showing a center LED activated). In addition, the power button 102 may alternately be toggled between cross-polarized and any other polarization state (i.e. parallel polarized or any polarization in between cross-polarized and parallel polarized). The alternate toggle state may be set by turning the polarization dial until the desired alternative polarization state is reached and then simultaneously holding down the UV button 104 and the and pigment boost button 106 for two (2) seconds to save this polarization state as the new default alternate toggle setting. Another way to incrementally toggle between cross polarized mode, non-polarized mode and parallel polarized mode, and all points in between, when the power button 102 has been activated, a user may turn the polarizer dial 74. In operation, the power button 102 is tapped, defaulting to cross polarized mode. If the user turns the polarizer dial clockwise, there will be no effect. However, if the user turns the polarizer dial counterclockwise the polarization will gradually change to reach non-polarized mode and parallel polarization at the far extreme. At any point after turning the dial 74 counterclockwise, the user can move the dial 74 clockwise to move back to a previous polarization, including back to the far extreme of cross polarization. Holding the power button 102 for one second turns the power to the device off. Also, tapping the power button 102 and holding the button 102 while turning the dial 74 adjusts the brightness of the white LEDs (not shown in FIGS. 6-11) in the head 68 of the device 60. The microprocessor may store in an on board non-transitory memory the level of brightness of white LEDs, and upon the next initiation of the button 102, the white LEDs will light at the same brightness.

A UV mode button 104 is provided on the right side of the housing 66 of the device 60 to enable UV LEDs (not shown in FIGS. 6-11) in the head 68 to activate. The UV LEDs operate to the exclusion of any other LEDs in the head 68. For example, if the power button 102 is activated, operating in cross-polarized mode for example, the tapping of UV mode button 104 will deactivate all other LEDs and turn on only the UV LEDs. Also, tapping the power button UV mode button 104 and holding the button 104 while turning the dial 74 adjusts the brightness of the UV LEDs. The microprocessor may store in an on board non-transitory memory the level of brightness of UV LEDs, and upon the next initiation of the button 104, the UV LEDs will light at the same brightness.

A pigment boost button 106 is provided on the right side of the housing 66 of the device 60 to enable orange and while LEDs (not shown in FIGS. 6-11) in the head 68 to activate. The orange and while LEDs operate to the exclusion of any other LEDs in the head 68. For example, if the power button 102 is activated, operating in cross-polarized mode, the tapping of pigment boost mode button 106 will deactivate all other LEDs and turn on only the orange and white LEDs to operate in pigment boost mode that enhances viewing of pigmented tissue and lesions. A thorough discussion of the use of orange LEDs in dermatoscopes may be found in U.S. Pat. No. 9,458,990, issued Oct. 4, 2016 to Mullani entitled Dermoscopy Illumination Device With Selective Polarization And Orange Light For Enhanced Viewing of Pigmented Tissue. Also, tapping the power button pigment boost mode button 106 and holding the button 106 while turning the dial 74 adjusts the brightness of the orange and white LEDs. The microprocessor may store in an on board non-transitory memory the level of brightness of orange and white LEDs when operating in pigment boost mode, and upon the next initiation of the button 106, the orange and white LEDs will light at the same brightness.

On the proximal side of the device 60, an elongate ferritic stainless steel ruler 92 is attached to the handle 70. A recess with embedded magnets to attract and attach the ruler 92 is provided. In addition, a space is provided on the handle 70 below the ruler 92 to allow a user to push down on the ruler to create a slight deformation so that the ends of the rule 92 may bend upward to allow a user to easily access and remove the ruler 92. The ruler may be used by the medical practitioner for any purpose, including the potential measuring of skin lesions. In addition, a measurement indicia 94 is screened or etched on to the glass of the faceplate 96 to provide the user a measurement aid when viewing features through the optics of the device.

Figure 12:
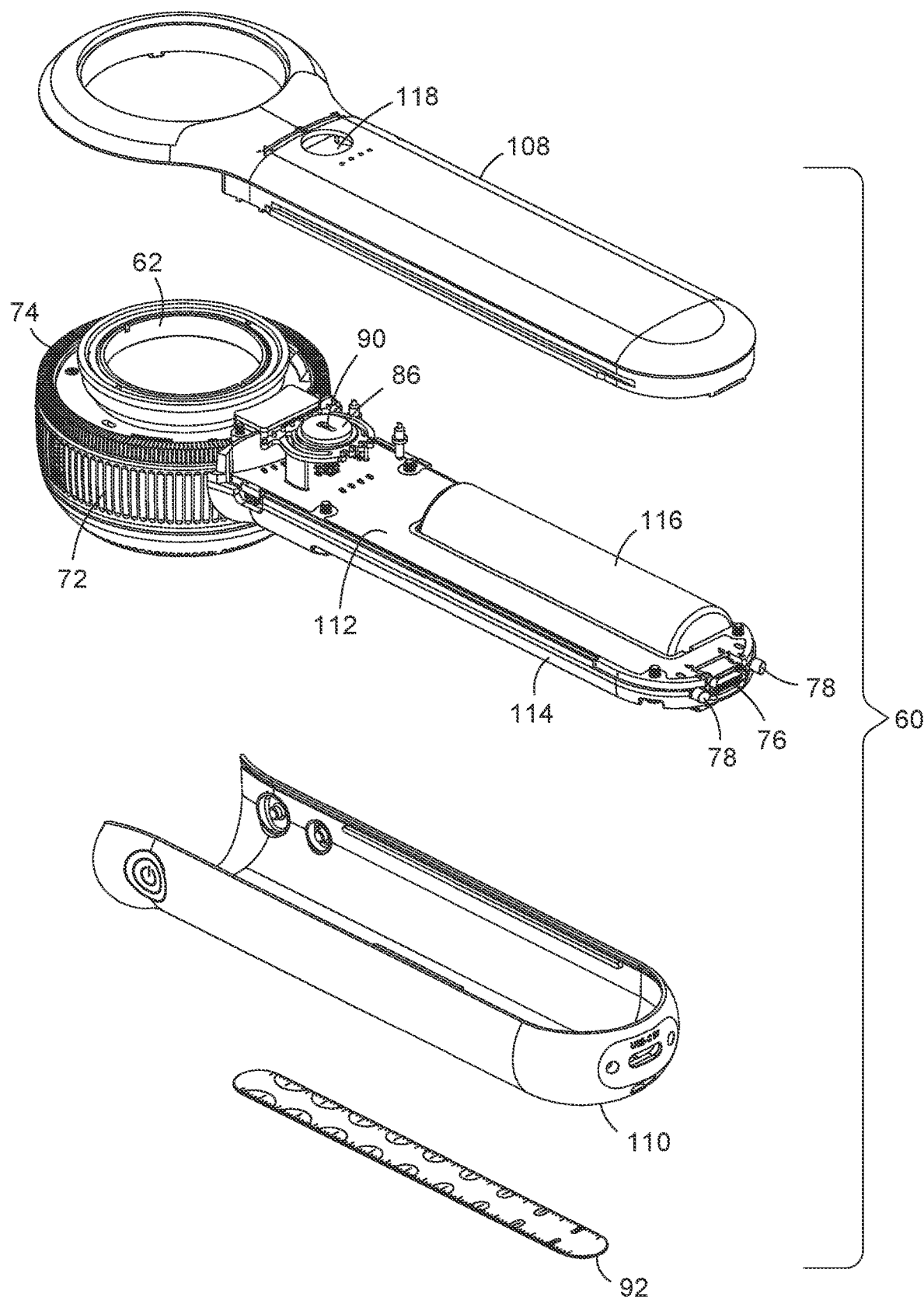
FIG. 12 is a perspective view with the housing exploded from internal components of the device according to the further embodiment.

Referring particularly to FIG. 12 there is shown an exploded view of the housing 66 from the internal components of the device 60. The housing 66 comprises a base cover 108 and handle cover 110. Also shown is the ruler 92 separated from the handle cover 110. The internal components include the main PCB 112 and mail PCB cover 114. A battery 116 nests within the PCB cover 114 and adjacent the PCB board 112 and the battery 116 is electrically interconnected to the power port 76 and contacts 78 for charging. The battery 116 also provides power to the electrical components of the device 60. The battery 116 is a lithium polymer rechargeable battery, however it is understood that any suitable battery type power source may be used in relation to the device 60. An aperture 118 is formed into the base cover 108 to provide exposure to the torch button. Light pipes (not shown) or other light transmitting mechanism may be formed on the interior of the base cover 108 to transmit light from LEDs located on the main PCB board 112 to provide visible light to the indicators such as polarizer indicator bar 82, battery status indicators 84, torch indicators 90, pigment boost mode indicator 98 and UV light indicators 100. The dial 74 is free to rotate below the base cover 108.

Figure 13:
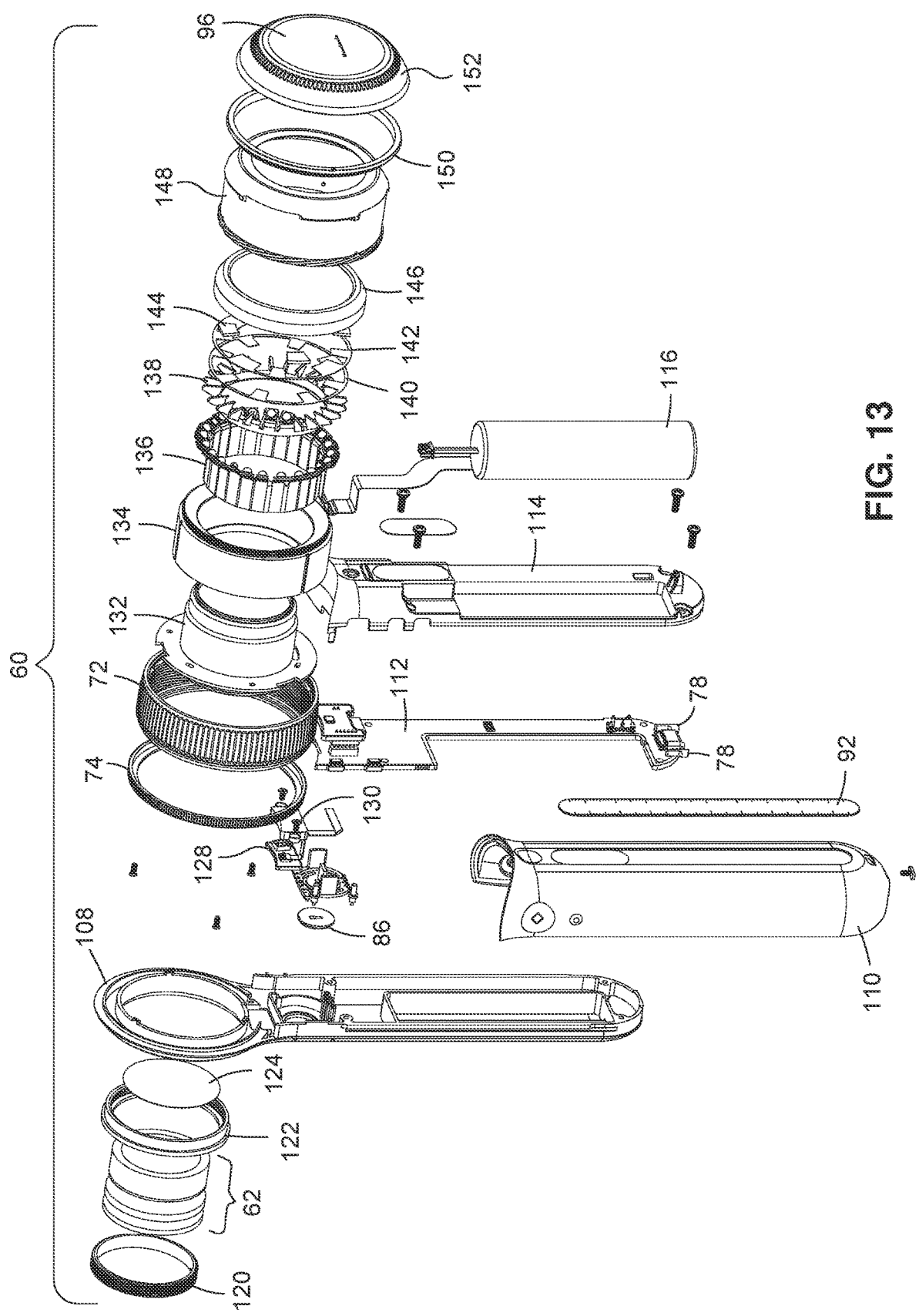
FIG. 13 is a perspective view with the interior and exterior components of the device exploded according to the further embodiment.
Figure 14:
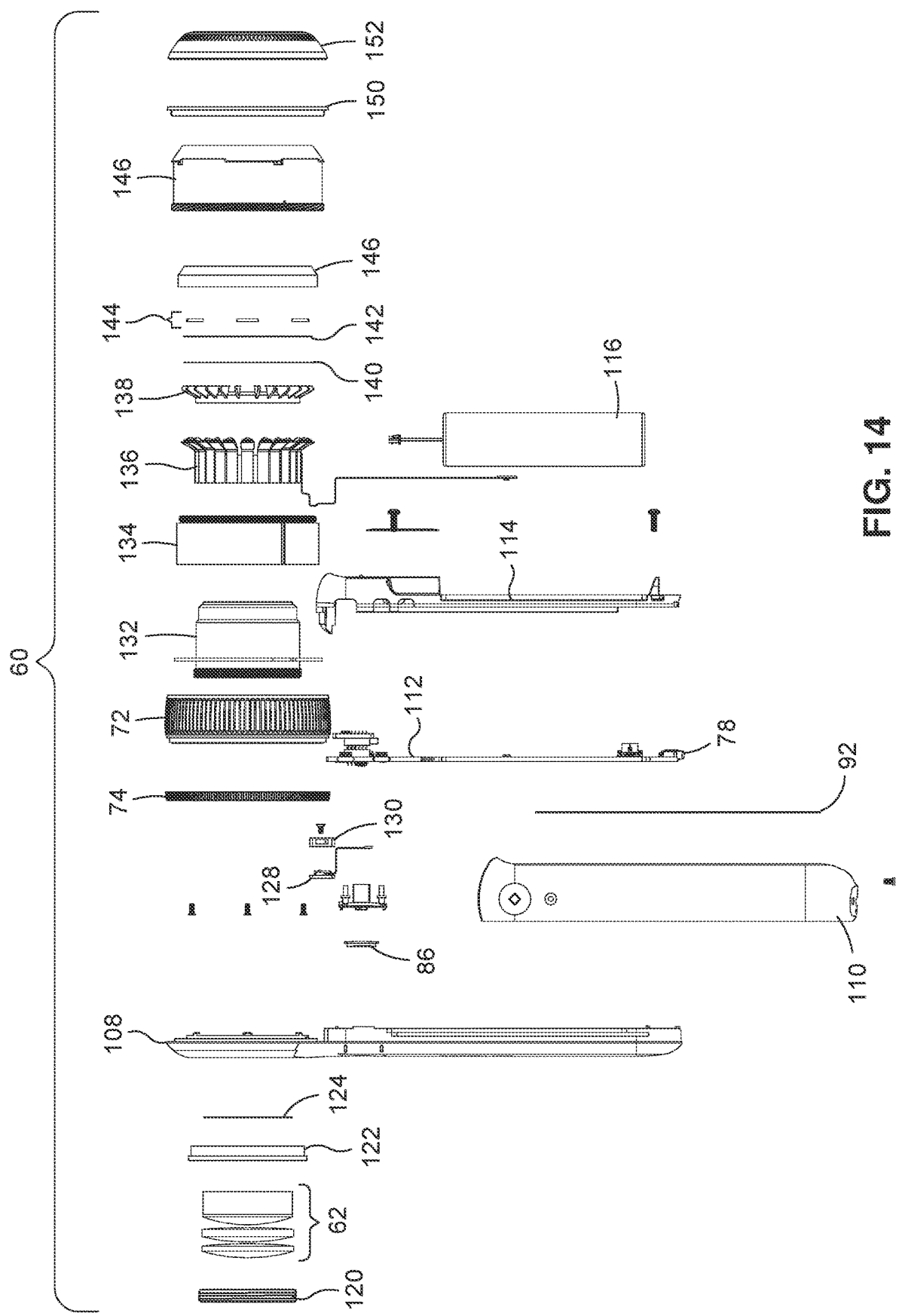
FIG. 14 is a side view with the interior and exterior components of the device exploded according to the further embodiment.

Referring particularly to FIGS. 13 and 14 there are shown exploded views of the of the components of the device 60 demonstrating the assembly of the such components. The exploded view of FIG. 13 is a perspective view, and FIG. 14 is a direct side view of the same exploded view of FIG. 13. Moving from the proximal end to the distal end, the components are identified as follows: lens retainer 120, lenses 62, lens tube retainer 122, center polarizer 124, base cover 108, torch button 86, dial PCB 128, dial PCB cover 130, polarization dial 74, spacer dial 72, main PCB 112, lens tube 132, PCB cover 114, LED base 134, LED PCB assembly 136, LED fin 138, battery 116, parallel polarizer 140, cross polarized polarizer 142, UV filters 144, LED base cap 146, spacer 148, spacer dial cap 150, face plate ring 152, face plate 96, handle cover 110 and rule 92. It is noted that the position of the parallel polarizer 140 and cross polarizer 142 are interchangeable since they are stacked upon one another, and the polarizers do not interfere with each other due to coordinated spacings of openings, described in more detail with regard to FIG. 21.

Figure 9:
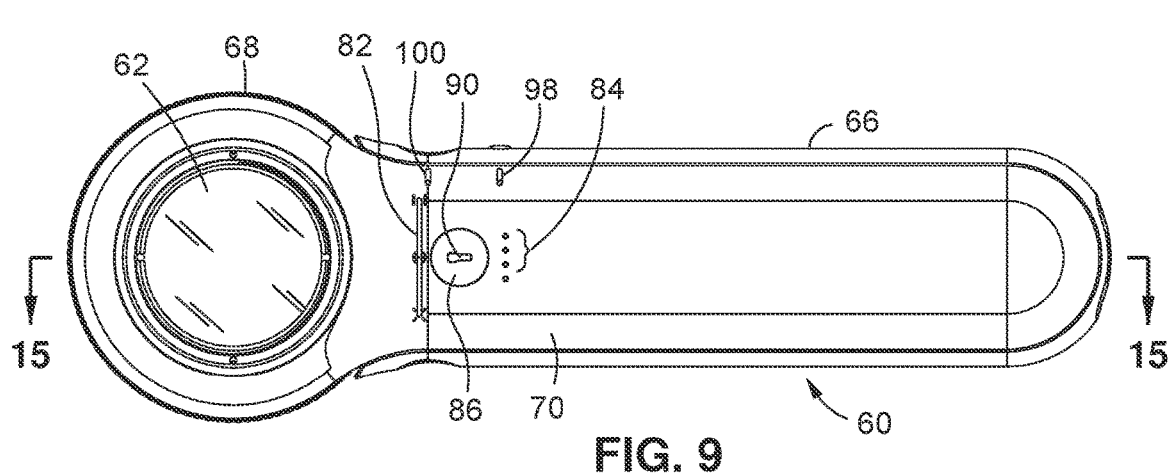
FIG. 9 is top view of the device according to the further embodiment.
Figure 10:
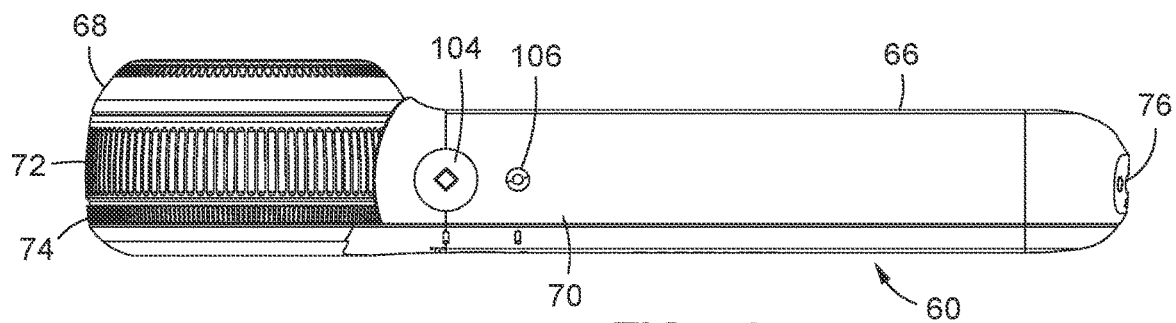
FIG. 10 is a right side view of the device according to the further embodiment.
Figure 11:
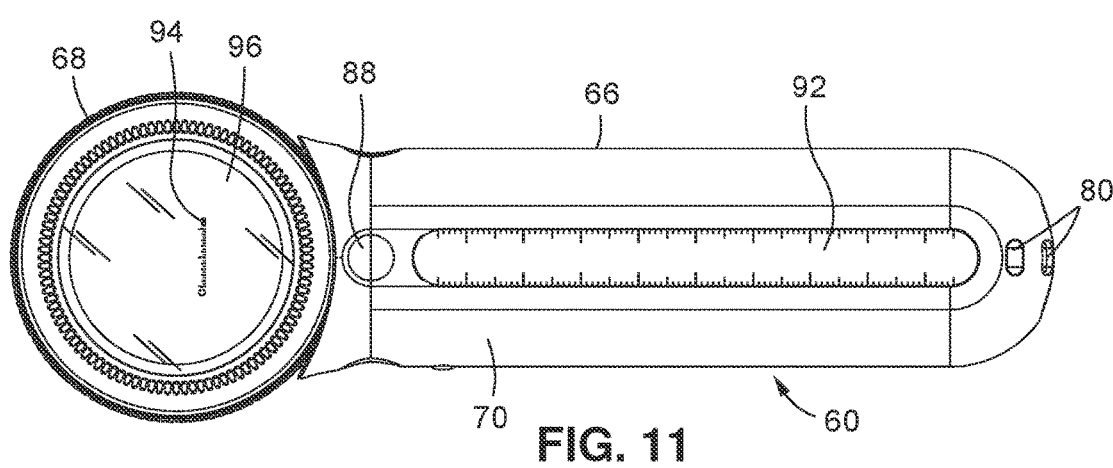
FIG. 11 is bottom view of the device according to the further embodiment.
Figure 15:
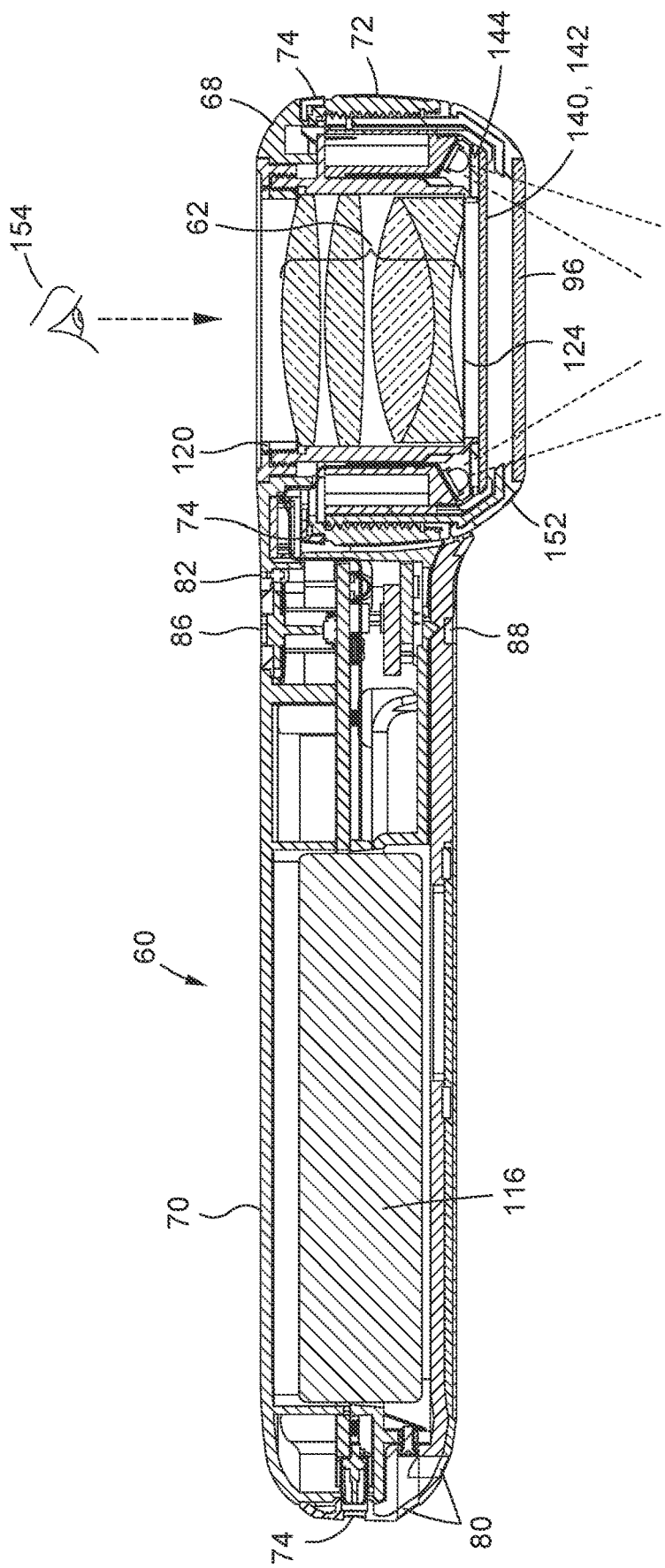
FIG. 15 is a cross sectional view of the device according to the further embodiment along the lines of 15-15 of FIG. 9.

Referring particularly to FIG. 15 there is shown a cross sectional view along lines 15-15 shown in FIG. 9. FIG. 15 demonstrates the position of the viewer 154 to view items located on the proximal side of the device, with the viewer 154 positioned on the distal side of the device, having an open view through the a lens assembly that includes lenses 62 arranged to provide a magnified view of the tissue to be examined. The lenses are preferably 10× magnification. The disclosed device lenses 62 is comprised of a compound lens with four spherical glass elements. While the device disclosed herein contemplates use of a compound lens with four spherical glass elements, other types of lenses, such as aspherical or those with polymer materials may be employed. The material for the lenses 62 may be molded PMMA with a hard coat surface. Other suitable material may also be used for the lenses 62.

Referring to FIG. 16 there is shown the LED PCB assembly 136 prior to assembly. The PCB board comprises 24 LEDs, LEDS D1 through D24. The LEDS comprise different types of LEDs. LEDs D3, D6, D9 and D12 comprise UV LEDs having an output of about 365 nm. As described herein with regard to other figures, LEDs D3, D6, D9 and D12 are not polarized, but emit light through an ZWB2 glass filter. LEDs D1, D13, D4, D16, D7, D19, D10 and D22 comprise white light LEDs. LEDs D1, D13, D4, D16, D7, D19, D10 and D22 as described herein with regard to other figures, emit light through a polarizer to emit cross-polarized light. LEDs D2, D5, D8, D11, D14, D17, D20 and D23 also comprise white light LEDs. LEDs D2, D5, D8, D11, D14, D17, D20 and D23 as described herein with regard to other figures, emit light through a polarizer to emit parallel-polarized light. LEDs D24, D21, D18 and D15 comprise orange light LEDs emitting light approximately in the range of 590 nm. LEDs D24, D21, D18 and D15 as described herein with regard to other figures, emit light through a polarizer to emit cross-polarized light.

Figure 19:
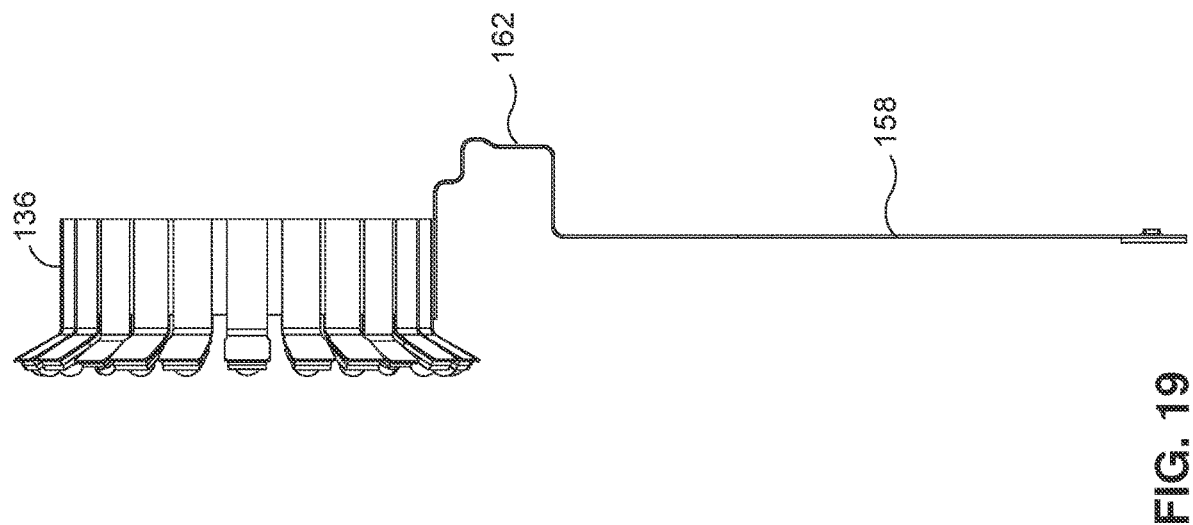
FIG. 19 is a side view of the LED ring printed circuit board assembly of the device according to the further embodiment.
Figure 18:
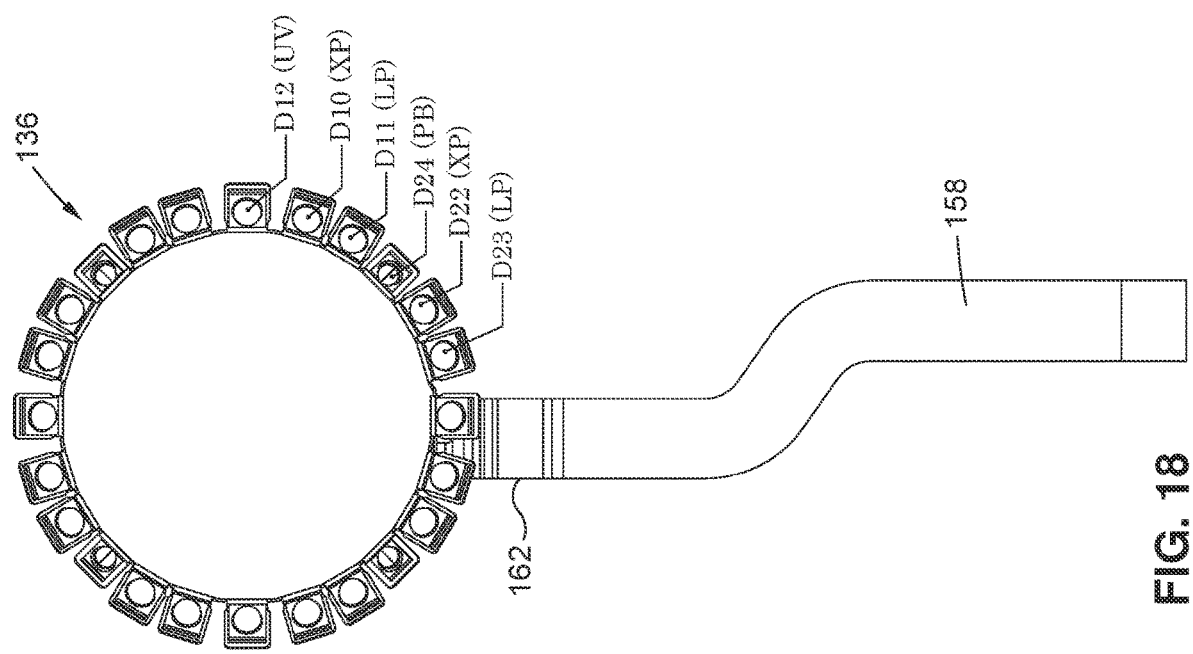
FIG. 18 is a bottom view of the LED ring printed circuit board assembly of the device according to the further embodiment.

The PCB board 136 as shown in FIG. 16 is prior to assembly, to form the PCB board 136 LED ring as shown in FIGS. 17-19. The LED portion 156 has the LEDs bonded on the PCB board each on fingers extending from the LED portion 156, wherein the LEDs are in electrical communication with the lead portion 158. The LED portion 156 is looped and connected at connection points 160 to form a ring. The fingers are angled outwardly from the ring at a 30-degree angle to expose the LEDs to direct light in the desired direction for positioning in the device 60. The lead portion 158 is formed to provide an electrical pathway within the device to avoid internal components by forming a pathway recess 162 as shown from the side in FIG. 19. Referring to FIG. 18 once the LED filters are put in place, the references to the LEDs are as follows: LEDs D23 (parallel polarized white light), D22 (cross polarized white light), D24 (cross polarized orange light), D11 (parallel polarized white light), D10 (cross polarized white light) and D12 (UV light with glass filter ZWB2). This pattern is repeated four times along the length of the LED circle 136.

Figure 21:
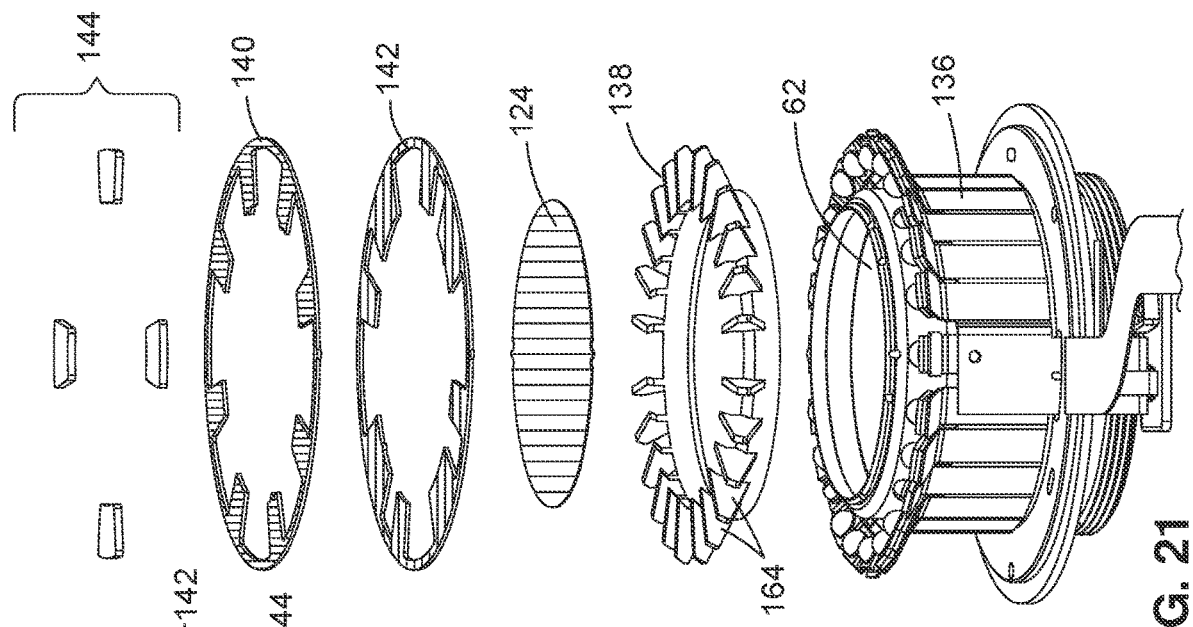
FIG. 21 is a view of the assembled components of FIG. 20 with the LED polarizers and filters along with the center polarizer exploded therefrom according to the further embodiment.
Figure 20:
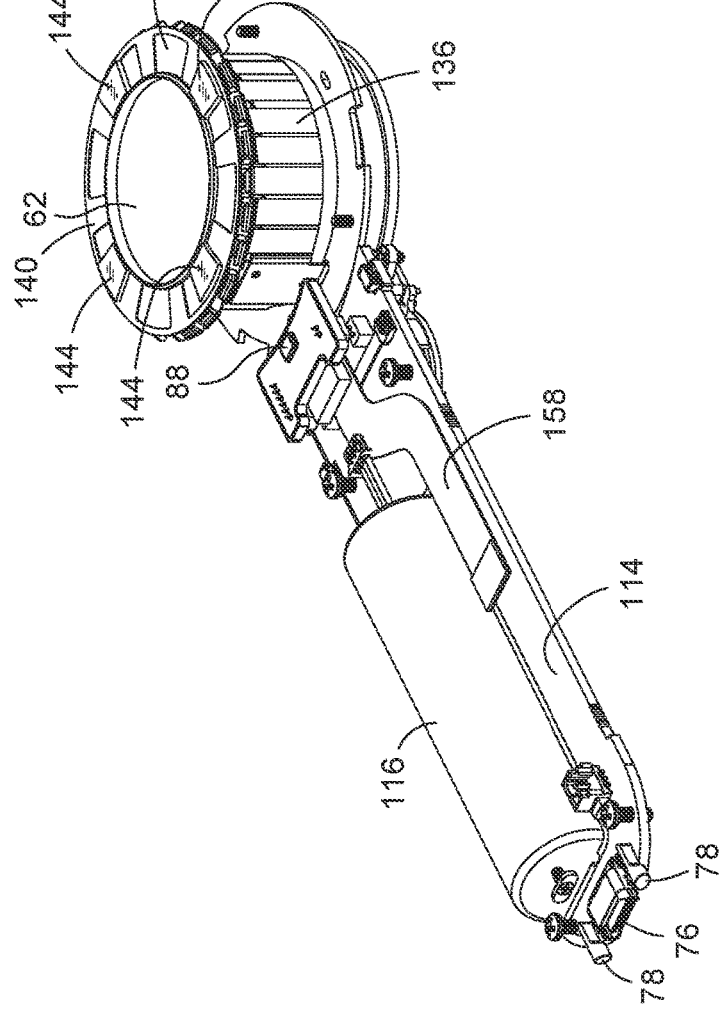
FIG. 20 is a side perspective view of the LED ring printed circuit board assembly with a fin LED separator attached to the main printed circuit board and printed circuit board cover with the LED polarizers and filters placed over the LEDs according to the further embodiment.

Referring particularly to FIG. 20 there is shown the LED ring 136 attached to the main PCB 114 with lead portion 158 electrically interfacing with the main PCB 114 so that the LEDs are in electrical communication with the items on the PCB board, including one or more microprocessors and battery 114 for power to the LEDs. Referring to FIG. 21 there is shown the fin 138 that engages the LED ring 136 and provides separation and fin walls 164 to create chambers for each LED to avoid light leakage between chambers. The fin 138 also provides a surface for filters 142, 140 and 142 to lay upon and to be fixed over each LED of the LED ring 136. The fins 164 may also be formed of a heat dissipating material and the fins 164 have surface areas to operate as a heat sink. A center polarizer 12 placed over the lenses 162 to polarize any light received from an object to be viewed.

Filter layers are placed over the LEDs and include the following: a cross polarizer 142 having a circular structure and a number of openings and filter areas to cover some of the LEDs and the openings not covering other LEDs. The cross polarizer 142 has a polarization and is positioned in the device 60 to be orthogonal to the center polarizer 124. The lines in FIG. 21 demonstrate the polarization orientation. Cross polarizer 142 covers and polarizes white LEDs D1, D4, D7, D10, D13, D16 and D19 and also covers and polarizes orange LEDs D12, D18, D21 and D24. The Cross polarizer 142 has openings and does not cover or polarize white LEDs D2, D5, D8, D11, D14, D17, D20 and D23 and also does not cover or polarized UV LEDs D3, D6, D9 and D12.

A parallel polarizer 140 is polarized in the same orientation as the center polarizer 124. The parallel polarizer 140 has a circular structure and a number of openings and filter areas to cover some of the LEDs and not covering other LEDs. The parallel polarizer 140 covers and polarizes eight white LEDs D2, D5, D8, D11, D14, D17, D20 and D23. The parallel polarizer 140 does not cover or polarize eight white LEDs D1, D4, D7, D10, D13, D16 and D19 and also does not cover or polarize four orange LEDs D12, D18, D21 and D24. The parallel polarizer 140 also does not cover or polarized UV LEDs D3, D6, D9 and D12.

The four UV LEDs are each covered by ZWB2 glass filters 144. The ZWB2 filter is a bandpass filter to filter the light emitted from the UV LEDs. The utilized bandpass filter for a particular LED attenuates all or a significant portion of frequencies outside of a desired frequency. Bandpass filters are placed over the light transmitting LED and may transmit a desired frequency range through the filter, while blocking all or most of certain frequency ranges of light from passing through the filter. In the further embodiment of the device, a ZWB2 bandpass filter is used. Use of ZWB2 bandpass filters result in much better contrast in an image due to the elimination of all or a significant portion of visible light. Although an embodiment of the device discloses a ZWB2 filter, it is contemplated by the present disclosure that other bandpass filters may be utilized that have a similar effect of a ZWB2 namely an optical filter that has higher transmittance in the UV spectrum than the visible spectrum. The embodiment of the device discloses the use of a ZWB2 bandpass filter offered by Optima, Inc. of Tokyo Japan. Optima offers optical filters under the designations ZBW1, ZBW3 and ZB1 having similar characteristics as a bandpass filter, blocking some wavelengths of light and the disclosure contemplates use of such filters. In addition, other manufactures offer filters having near characteristics of the ZWB2 filter, namely Hoya Corporation of Tokyo, Japan offers U-360 and UL365 Glass filters and Schott North America, Inc of Duryea, Pa. offer a product under the designation of UG11. Hoya also offers U-340 and U-330 glass filters that may be used and other Schott products under the designations UG1 and UG5 are contemplated by the disclosure.

The filters 142 and 140 are overlaid onto the fin 138 so that they are stacked. Because the filters 142 and 140 have complementary openings and coverings, so that when placed in the proper position will not interfere or overlap with each other. In this regard, the filters 142 and 140 are reversable in stacking order, and as shown in FIG. 21, the cross-polarizing filter 142 is placed directly over the fin 138 and the parallel polarizer 140 is overlaid on top of the cross polarizing filter 142. After filters 140 and 142 are positioned, there are openings for the LEDs D3, D6, D9 and D12, over which the ZWB2 filters 144 are placed.

Referring to FIGS. 22, 23 and 24 there is shown components related to the operation of the electronics with the dial 74. A dial PCB 128 positioned on the lead portion 158. On the side of dial PCB 128 closest to the dial 74 a reflective encoder 166 (shown in FIG. 22) is positioned and pointed to the dial 74 and particularly to the dial bottom 168 for optical rotation detection of the dial 74. The reflective encoder 166 is an Avago AEDR-8300 module manufactured by Avago Technologies of San Jose, Calif., USA. The encoder 166 emits infrared signals and one or more optical readers on the encoder 166 detects reflection and can detect movement of the dial 74 by the lines or striations included on the dial bottom 168. On dial 74 there are 212 lines per inch enabling detection of slight movement. Detecting rotation, the encoder sends signals to a microprocessor (not shown) regarding the position of the dial.

Referring to FIG. 25 there is shown the top view of the LED assembly 136, with filters 140, 142 and 144 overlaying the LEDs. The LEDs are shown and identified. The following is a listing of the LEDs with their respective wavelengths and polarizations. LEDs D1, D4, D7, D10, D13, D16 and D19 are white light LEDs and due to the location of the cross polarizer 142 emit white cross-polarized light. LEDs D12, D18, D21 and D24 are orange LEDs with a wavelength of about 590 nm, and due to the location of the cross-polarizer, such LEDs emit orange cross-polarized light. LEDs D2, D5, D8, D11, D14, D17, D20 and D23 are white light LEDs and due to the location of the parallel polarizer 140 emit parallel polarized white light. LEDs D3, D6, D9 and D12 are UV LEDs and with the placement of ZWB2 filters 144, such LEDs emit UV light modified by the bandpass filters. The positioning of different wavelength LEDs, filters and polarizers allows for the operation of the device 60 to emit variable polarization and operate in a plurality of modes.

Figure 26:
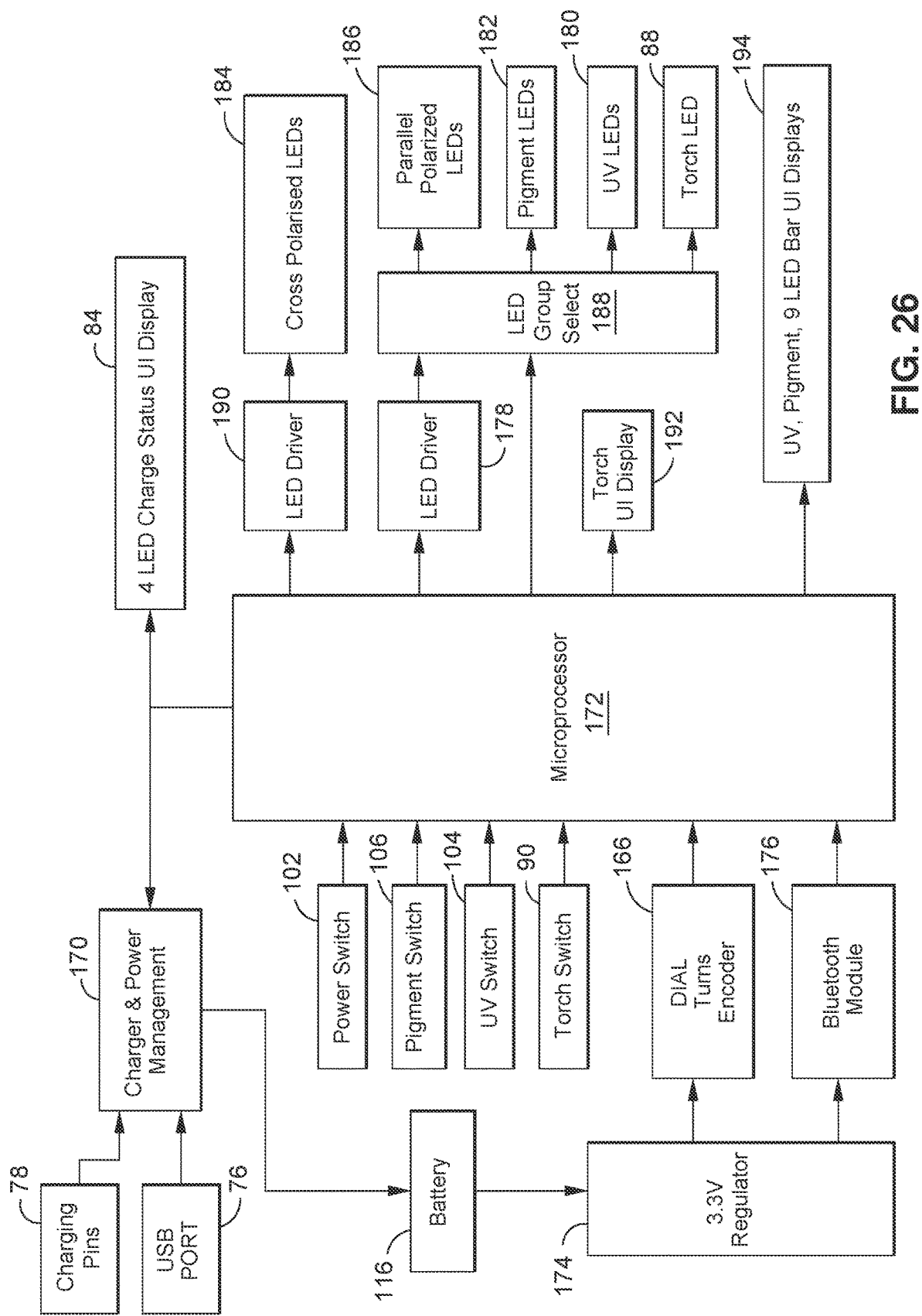
FIG. 26 is a schematic view of the device showing circuit components for operating the device according the second embodiment.

Referring to FIG. 26 is a schematic of the electronic components of the device 60. The USB port 76 and charging pins 78 may supply power to the device 60 through a power management circuit 170 which may be an integrated circuit chip. The circuit 170 may manage power input to supply power for charging the battery 116 and to provide signals to light the LED charge display 84. Also, the circuit may manage power to a microprocessor 172. The microprocessor 172 received input from various sources, and depending on input, may drive various elements as a result. The battery 116 also supplies power to a 3.3v regulator that provides sufficient power to at least the encoder 166 and/or a Bluetooth module 176. The Bluetooth module 176 enables the device 60 to be wirelessly coupled to an external device (e.g. a smartphone or other mobile device) via radio frequency transmission according to any of various wireless communication protocol, including Bluetooth. A mobile application may operate in place of the manual switches, allowing a user to implement the various modes by wirelessly communicating with the microprocessor 172 from an external device. As such, a user may selectively drive the LEDs of the device 60 in order to increase or decrease the effective penetration depth when viewing organic tissue by manipulating the cross polarized and parallel polarized light to simulate variable polarization as would be achieved by rotating one or more polarizers, wherein the device 60 polarizers remain stationary.

In device 60 there are three modes of operation that are independent of variable polarization. The first flashlight mode involves the torch switch 90 which initiates and deactivates a flashlight type LED 88 that is not associated with any polarizers. The signal from the torch switch 90 is received by the microprocessor 172 and a signal is sent to the LED driver 178 to drive the torch LED 88 and may activate or deactivate user interface torch display 192 to let the user know the state of the torch mode. When a user holds down the torch switch 90 while simultaneously turning the polarization dial 74, the brightness of the torch LED 88 may be adjusted, and the level of brightness saved in the system memory. Turning of the dial 74 effects the encoder 166 that provides a signal to the microprocessor indicating the position of the dial for determining brightness of the torch LED 88 and sending a signal to LED driver 178 to adjust the brightness.

In a further UV mode, switch 104 initiates and deactivates the UV LEDs (comprising LEDs D3, D6, D9 and D12) and the UV light emitted is filtered through a bandpass filter 144. The signal from the UV switch 104 is received by the microprocessor 172 and a signal is sent to the LED driver 178 to drive the UV LEDs 180 and may activate or deactivate user interface mode display 194 to let the user know the state of the UV mode. When a user holds down the UV switch 104 while simultaneously turning the polarization dial 74, the brightness of the UV LEDs may be adjusted, and the level of brightness saved in the system memory. Turning of the dial 74 effects the encoder 166 that provides a signal to the microprocessor indicating the position of the dial for determining brightness of the UV LEDs and sending a signal to the LED driver 178 to adjust brightness.

In a further pigment boost mode, pigment switch 106 initiates and deactivates both the orange pigment LEDs 182 (comprising LEDs D3, D6, D9 and D12) and white cross polarized LEDs 184 (comprising LEDs D1, D4, D7, D10, D13, D16 and D19), and the light emitted from the orange and white LEDs is cross polarized. The signal from the pigment switch 104 is received by the microprocessor 172 and a signal is sent to the LED drivers 190 and 178 to drive the white cross polarized LEDs 184 and pigment LEDs 182, respectively and may activate or deactivate user interface mode display 194 to let the user know the state of the pigment boost mode. When a user holds down the pigment switch 106 while simultaneously turning the polarization dial 74, the brightness of the orange LEDs may be adjusted, and the level of brightness saved in the system memory. Turning of the dial 74 effects the encoder 166 that provides a signal to the microprocessor indicating the position of the dial for determining brightness of the orange LEDs. The microprocessor 172 is capable of directing grouping of the parallel LEDs 186, pigment LEDs 182, UV LEDs 180 and/or torch LED 88 through an LED group select 188 circuit.

In variable polarization mode, the user initiates power switch 102, and the device 60 defaults to cross polarization mode wherein white light LEDs 184 (comprising D1, D4, D7, D10, D13, D16 and D19) are activated and the light emitted from the white LEDs 184 is cross polarized. The signal from the power switch 102 is received by the microprocessor 172 and a signal is sent to the LED driver 190 to drive the white cross polarized LEDs 184 and may activate or deactivate user interface mode display 194 to let the user know the state of polarization by the LED bar 82. By turning the dial 74 counterclockwise, the encoder 166 senses movement of the dial, and sends sensor information to the microprocessor 172 so that the sensor can activate to determine the intensity for initiating both the white cross polarized light LEDs 184 (comprising D1, D4, D7, D10, D13, D16 and D19) through driver 190 and the white parallel polarized LEDs 186 through driver 178. For example, if the dial 74 is turned 10%, the cross polarized LED 184 intensity is at 90% and the parallel polarized LED 186 is at 10% simulating variable polarization. In this regard, whatever percentage movement of the dial 74 in the clockwise direction, the intensity of the light for the cross polarized LEDs 184 is the inverse of that percentage. At the midpoint for turning the dial 74, the LEDs 184 and 186 are at equal intensity, and thus simulate non-polarized light. In this way, by manipulating the inverse percentage of intensity between LEDs 184 and 186, the variable polarization mode simulates the mechanical movement of a polarizer.

In a variation of the variable polarized mode, a user may tap on the power switch 102 to toggle between cross-polarized mode (100% intensity of cross polarized LEDs 184) and non-polarized mode (50% intensity of cross polarized LEDs 184 and 50% intensity parallel LEDs 186). In a further non-variable polarized mode using the power button 102, a user can hold the power button 102 while simultaneously turning the dial 74 to adjust the brightness of the white LEDs 184 and white LEDs 186.

Throughout the disclosure, the term "parallel polarized" is interchangeable with "linear polarized" and also is intended to encompass co-polarized light in the case of circular or elliptical polarization. By the same token, the "first polarization direction" and "second polarization direction" may refer to circular or elliptical directions (e.g. left-handedness, right-handedness) as well as linear directions.

The above description is given by way of example, and not limitation. Given the above disclosure, one skilled in the art could devise variations that are within the scope and spirit of the disclosure herein. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An illumination device for illuminating organic tissue, the illumination device comprising:
   a first set of one or more light emitting diodes (LEDs);
   a first polarizer arranged to polarize light emitted from the first set of one or more LEDs in a first polarization state;
   a second set of one or more LEDs;
   a second polarizer arranged to polarize light emitted from the second set of one or more LEDs in a second polarization state;
   a lens arranged to collect light from organic tissue illuminated by either one or both of the first and second sets of one or more LEDs;
   a viewing polarizer arranged to polarize the light collected from the organic tissue in the second polarization state;
   one or more drivers for driving one of the first and second sets of one or more LEDs according to a first signal and driving the other of the first and second sets of LEDs according to a second signal; and
   a microprocessor operable to generate the first signal as a function of a user input value and to generate the second signal as a function of the same user input value.

2. The illumination device of claim 1 wherein, for a given change in the user input value, the first and second signals vary oppositely to each other.

3. The illumination device of claim 2 wherein the first and second signals are pulse width modulation (PWM) signals.

4. The illumination device of claim 3 wherein the microprocessor is operable to generate the first and second signals such that the first signal has a maximum duty cycle and the second signal has a minimum duty cycle for the same user input value.

5. The illumination device of claim 2 wherein the first and second signals are continuous current signals.

6. The illumination device of claim 5 wherein the microprocessor is operable to generate the first and second signals such that the first signal has a maximum current value and the second signal has a minimum current value for the same user input value.

7. The illumination device of claim 1 wherein the first and second signals are pulse width modulation (PWM) signals.

8. The illumination device of claim 7 wherein the microprocessor is operable to generate the first and second signals such that the first signal has a maximum duty cycle and the second signal has a minimum duty cycle for the same user input value.

9. The illumination device of claim 1 wherein the first and second signals are continuous current signals.

10. The illumination device of claim 9 wherein the microprocessor is operable to generate the first and second signals such that the first signal has a maximum current value and the second signal has a minimum current value for the same user input value.

11. The illumination device of claim 1 further comprising a dial, the user input value being derived from a change in position of the dial.

12. The illumination device of claim 11 further comprising an optical encoder configured to detect the change in the position of the dial.

13. An illumination device for illuminating organic tissue, the illumination device comprising:
   a first set of one or more light emitting diodes (LEDs);
   a first polarizer arranged to polarize light emitted from the first set of one or more LEDs in a first polarization direction;
   a second set of one or more LEDs;
   a second polarizer arranged to polarize light emitted from the second set of one or more LEDs in a second polarization direction;
   a lens arranged to collect light from organic tissue illuminated by either one or both of the first and second sets of one or more LEDs;

a viewing polarizer arranged to polarize the light collected from the organic tissue in the second polarization direction;

a pulse generator operable to generate a pulsed voltage having an adjustable pulse width; and one or more drivers for driving one of the first and second sets of one or more LEDs according to the pulsed voltage and driving the other of the first and second sets of one or more LEDs according to an inverse of the pulsed voltage.

14. The illumination device of claim 13 further comprising a dial whose position determines a user input value for adjusting the adjustable pulse width.

15. The illumination device of claim 14 further comprising an optical encoder configured to generate the user input value from the position of the dial.

* * * * *